(12) United States Patent
Carruthers et al.

(10) Patent No.: US 8,829,011 B2
(45) Date of Patent: Sep. 9, 2014

(54) 2-AMINOPYRIMIDINE COMPOUNDS AS SEROTONIN RECEPTOR MODULATORS

(75) Inventors: Nicholas I. Carruthers, Poway, CA (US); Gregor J. MacDonald, Beerse (BE); Brock T. Shireman, Poway, CA (US); Vi T. Tran, Irvine, CA (US)

(73) Assignee: Janssen Pharmaceutica NV, Beerse (BE)

( * ) Notice: Subject to any disclaimer, the term of this patent is extended or adjusted under 35 U.S.C. 154(b) by 403 days.

(21) Appl. No.: 13/126,205

(22) PCT Filed: Oct. 29, 2009

(86) PCT No.: PCT/US2009/062486
§ 371 (c)(1),
(2), (4) Date: Apr. 27, 2011

(87) PCT Pub. No.: WO2010/053825
PCT Pub. Date: May 14, 2010

(65) Prior Publication Data
US 2011/0207717 A1    Aug. 25, 2011

Related U.S. Application Data

(60) Provisional application No. 61/109,262, filed on Oct. 29, 2008.

(51) Int. Cl.
| | | |
|---|---|---|
| C07D 471/04 | (2006.01) | |
| A61K 31/519 | (2006.01) | |
| C07D 519/00 | (2006.01) | |
| C07D 487/04 | (2006.01) | |
| A61P 25/28 | (2006.01) | |
| A61P 25/22 | (2006.01) | |
| A61P 25/24 | (2006.01) | |
| A61P 25/18 | (2006.01) | |

(52) U.S. Cl.
CPC ............ *C07D 487/04* (2013.01); *C07D 519/00* (2013.01); *C07D 471/04* (2013.01)
USPC ...... 514/264.11; 544/279; 544/122; 540/578; 540/600; 514/234.2

(58) Field of Classification Search
CPC ............................. C07D 471/04; A61K 31/519
USPC ..................................... 544/279; 514/264.11
See application file for complete search history.

(56) References Cited

U.S. PATENT DOCUMENTS

| | | | | |
|---|---|---|---|---|
| 5,137,890 A | * | 8/1992 | Sanfilippo et al. | ......... 514/264.1 |
| 7,598,255 B2 | | 10/2009 | Dvorak et al. | |
| 2007/0032481 A1 | | 2/2007 | Dvorak et al. | |

FOREIGN PATENT DOCUMENTS

| | | |
|---|---|---|
| WO | WO 01 44246 A1 | 6/2001 |
| WO | WO 02 14314 A2 | 2/2002 |
| WO | WO 2005 040169 A2 | 5/2005 |
| WO | WO 2008 117169 A1 | 10/2008 |

OTHER PUBLICATIONS

Banker, G.S. et al, "Modern Pharmaceutics, 3ed.", Marcel Dekker, New York, 1996, p. 596.*
Wolff, Manfred E. "Burger's Medicinal Chemistry, 5ed, Part I", John Wiley & Sons, 1995, pp. 975-977.*
Bagshawe et al. "Antibody-Directed Enzyme Prodrug Therapy: A Review" Drug Dev Res 1995 vol. 34 pp. 220-230.
Berge et al. "Pharmaceutical Salts". J. Pharm Sci 1977 vol. 66 pp. 1-19.
Bertolini et al. "A New Rational Hypothesis for the Pharmacophore of the Active Metabolite of Leflunomide, A Potent Immunosuppressive Drug" J Med Chem 1997 vol. 40 pp. 2011-2016.
Bodor et al. "Novel Approaches to the Design of Safer Drugs: Soft Drugs and Site-Specific Chemical Delivery Systems" Adv Drug Res 1984 vol. 13 pp. 224-331.
Bundgaard et al Design of Prodrugs H Bundgaard Ed. Elsevier 1985.
Cheng et al "Relationship Between the Inhibition Constant ($K_1$) and the Concentration of Inhibitor Which Cause 50 PE Cent Inhibition ($I_{50}$) of an Enzymatic Reaction" Biochem Pharmacol 1973 vol. 22 pp. 3099-3108.
Fleisher et al "Improved Review Oral Drug Delivery: Solubility Limitations of Prodrugs Overcome by the Use" Adv Drug Delivery Rev 1996 vol. 19 pp. 115-130.
Hoyer et al "Molecular, Pharmacological and Functional Diversity of 5-HT Receptors" Pharmacol Biochem Behav 2002 vol. 71 pp. 533-554.
Larsen et al Design and Application of Prodrugs, Drug Design and Development Krogsgaard-Larsen et al Harwood Academic Publishers 1991.
Paulekuhn et al "Trends in Active Pharmaceutical Ingredient Salt Selction Based on Analysis of the Orange Book Database" J Med Chem 2007 vol. 50 pp. 6665-6672.
Robinson et al "Discovery of the Hemifumarate and (A-L-Alanyloxy)Methyl Ether as Prodrugs of an Antirheumatic Oxindloe: Prodrugs for the Enolic OH Group" J Med Chem 1996 Vlume 39 pp. 10-18.

(Continued)

*Primary Examiner* — Susanna Moore
(74) *Attorney, Agent, or Firm* — Michael J. Atkins

(57) ABSTRACT

Certain 2-aminopyrimidine compounds of formula (I) are serotonin receptor modulators useful in the treatment of diseases mediated by serotonin receptors.

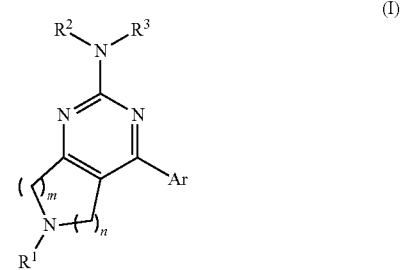

(I)

19 Claims, No Drawings

(56) References Cited

OTHER PUBLICATIONS

Roth et al "The Multiplicity of Serotonin Receptors: Useselly Diverse Moledcules or an Embarassment of Riches?" The Neuroscientist 2000 vol. 6(4) pp. 252-262.
Shan et al "Prodrug Strategies Based on Intramolecular Cyclizaton Reactions" J Pharm Sci 1997 vol. 86(7) pp. 765-767.
Stahl et al Essential Psychopharmacology 2000 2nd Ed Cambridge Univ Press Cambridge UK 2000.
Stahl and Wermuth Eds Handbook of Pharmaceutical Salts, Propeties, Selection, and Use Wiley-VCH and VHCA Zurich 2002.
Stolle et al "Intramolecular Diels-Alder Reactions of Pyrimidines: Synthesis of Tricyclic Annelated Pyridines" Tetrahedron 1989 vol. 45(20) pp. 6511-6518.
Sanfilippo "Novel Tetrahydropyrido[3,4-d]Pyrimidines as Gastric Antilesion Agents" Eur J Med Chem 1972 vol. 27 pp. 655-661.
International Search Report for Corresponding International Application PCT/US2009/062486 mailed on Feb. 4, 2010.

* cited by examiner

2-AMINOPYRIMIDINE COMPOUNDS AS SEROTONIN RECEPTOR MODULATORS

CROSS-REFERENCE TO RELATED APPLICATIONS

This application is a national phase of International Application No. PCT/US2009/062486 and claims benefit of priority under 35 U.S.C. §119(e) of U.S. Provisional Application No. 61/109,262 filed on Oct. 29, 2008.

FIELD OF THE INVENTION

The present invention relates to certain 2-aminopyrimidine compounds, pharmaceutical compositions containing them, and methods of using them for the treatment of disease states, disorders, and conditions mediated by serotonin receptor activity.

BACKGROUND OF THE INVENTION

Serotonin (5-hydroxytryptamine, 5-HT) is a major neurotransmitter eliciting effects via a multiplicity of receptors. To date, at least fifteen different 5-HT receptors have been identified, largely as the result of cloning cDNA's, and these receptors have been grouped into seven families (5-HT$_1$ through 5-HT$_7$) (Hoyer, D. et al. *Pharmacol. Biochem. Behav.* 2002, 71, 533-554).

Fourteen of the fifteen cloned 5-HT receptors are expressed in the brain. 5-HT is implicated in many disease states, particularly conditions of the central nervous system including; depression, anxiety, schizophrenia, eating disorders, obsessive compulsive disorder, learning and memory dysfunction, migraine, chronic pain, sensory perception, motor activity, temperature regulation, nociception, sexual behavior, hormone secretion, and cognition.

The identification of multiple 5-HT receptors has provided the opportunity to characterize existing therapeutic agents thought to act via the serotonergic system. Consequently, this has led to the realization that many drugs have non-selective properties (Roth, B. L. et al. *Neuroscientist* 2000, 6(4), 252-262). For example, the antipsychotic drugs, clozapine, chlorpromazine, haloperidol and olanzapine exhibit affinities for multiple serotonin receptors in addition to other families of receptors. Similar behavior has been noted for antidepressants, including imipramine, nortriptaline, fluoxetine and sertraline. Similarly, the anti-migraine agent sumatriptan exhibits high affinity for several serotonin receptors. While the lack of selectivity often contributes to a favorable therapeutic outcome, it can also cause undesirable and dose-limiting side effects (Stahl, S. M. *Essential Psychopharmacology*, 2$^{nd}$ ed., Cambridge University Press, Cambridge, U.K., 2000). Thus, the inhibition of serotonin and norepinephrine uptake together with 5-HT$_2$ receptor blockade is responsible for the therapeutic effects of the tricyclic antidepressants. In contrast, their blockade of histamine H$_1$, muscarinic and alpha-adrenergic receptors can lead to sedation, blurred vision and orthostatic hypertension respectively. Likewise, the atypical antipsychotics, including olanzapine and clozapine, are considered to have positive therapeutic effects attributable to their actions at 5-HT$_2$, D$_2$ and 5-HT, receptors. Conversely, their side effect liability is due to their affinities for a range of dopaminergic, serotonergic and adrenergic receptors.

More selective ligands therefore have the potential to ameliorate untoward pharmacologies and provide novel therapies. More importantly the ability to obtain compounds with known receptor selectivities affords the prospect to target multiple therapeutic mechanisms and improve clinical responses with a single drug. There remains a need for potent serotonin receptor modulators with desirable pharmaceutical properties.

4-Phenyltetrahydropyrido[4,3-d]pyrimidines with utility in the treatment of gastrointestinal diseases are described by Sanfilippo et al. in U.S. Pat. No. 5,137,890 and Eur. J. Med. Chem. 1992, 27(7), 655-661. Fused 2-aminopyrimidines have been disclosed as glycogen synthase kinase 3 (GSK3) inhibitors for the treatment of Alzheimer's disease and other neurodegenerative disorders, traumatic brain injury, and bipolar disorder in Intl. Pat. Appl. Publ. WO 2001/044246.

Indole and pyrazole compounds have been described as serotonin modulators in Intl. Pat. Appl. Publ. WO 2005/040169 (Janssen Pharmaceutica N.V., May 6, 2005). Pyrimidine compounds have been described as serotonin modulators in U.S. Pat. Appl. Publ. No. US 2007/032481 (Janssen Pharmaceutica N.V., Feb. 8, 2007).

SUMMARY OF THE INVENTION

Certain 2-aminopyrimidine derivatives have now been found to have serotonin receptor modulating activity. Thus, the invention is directed to the general and preferred embodiments defined, respectively, by the independent and dependent claims appended hereto, which are incorporated by reference herein.

In one general aspect the invention relates to a compound of the following Formula (I):

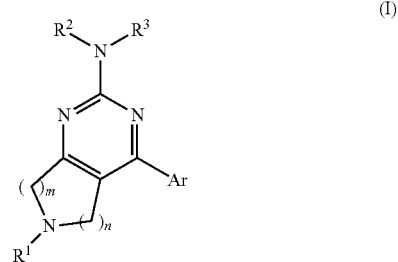

wherein
m is 1, 2, or 3;
n is 1, 2, or 3;
where m+n is greater than or equal to 2, and is less than or equal to 4;
R$^1$ is —H, —C$_{1-4}$alkyl, or benzyl;
R$^2$ and R$^3$ are each independently —H, —C$_{1-4}$alkyl, or benzyl;
or alternatively, R$^2$ and R$^3$ taken together with the nitrogen to which they are attached form a saturated monocyclic heterocycloalkyl ring, unsubstituted or substituted with one or two substitutents selected from —C$_{1-4}$alkyl, —OH, and halo;
Ar is a phenyl, monocyclic heteroaryl, or bicyclic heteroaryl ring, unsubstituted or substituted with one or two R$^i$ substituents;
R$^i$ is selected from the group consisting of —C$_{1-7}$alkyl, —C$_{2-7}$alkenyl, —C$_{2-7}$alkynyl, —C$_{3-7}$cycloalkyl, halo, —CF$_3$, —OH, —OC$_{1-7}$alkyl, —OCF$_3$, —OC$_{3-7}$alkenyl, —OC$_{3-7}$alkynyl, —N(R$^j$)R$^k$, —C(O)N(R$^j$)R$^k$, —N(R$^j$)C(O)R$^k$, —N(R$^j$)SO$_2$C$_{1-6}$alkyl, —S(O)$_{0-2}$—C$_{1-6}$alkyl, —SO$_2$N(R$^j$)R$^k$, —SCF$_3$, —C(O)C$_{1-6}$alkyl, —NO$_2$, —CN, —COOH, and —COOC$_{1-7}$alkyl;
where R$^j$ and R$^k$ are independently —H or —C$_{1-4}$alkyl;
or alternatively, two adjacent R$^j$ substituents form —OC$_{1-4}$alkyleneO—, —(CH$_2$)$_{2-3}$NH—, —(CH$_2$)$_{1-2}$NH(CH$_2$)—, —(CH$_2$)$_{2-3}$N(C$_{1-4}$alkyl)-, or —(CH$_2$)$_{1-2}$N(C$_{1-4}$alkyl)(CH$_2$)—;

with the proviso that when m is 2, n is 1, and Ar is phenyl, then $R^2$ and $R^3$ are not —H or —$C_{1-3}$alkyl;

or a pharmaceutically acceptable salt, a pharmaceutically acceptable prodrug, or a pharmaceutically active metabolite thereof.

In a further general aspect, the invention relates to pharmaceutical compositions each comprising: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

In another general aspect, the invention is directed to a method of treating a subject suffering from or diagnosed with a disease, disorder, or medical condition mediated by the serotonin receptors, particularly, 5-HT, and/or 5-$HT_2$ receptor subtypes, comprising administering to the subject in need of such treatment an effective amount of a compound of Formula (I), or a pharmaceutically acceptable salt, pharmaceutically acceptable prodrug, or pharmaceutically active metabolite thereof.

In certain preferred embodiments of the inventive method, the disease, disorder, or medical condition is selected from: cognitive disorders, sleep disorders, psychiatric disorders, and other disorders.

Additional embodiments, features, and advantages of the invention will be apparent from the following detailed description and through practice of the invention.

DETAILED DESCRIPTION OF THE INVENTION

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by /), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

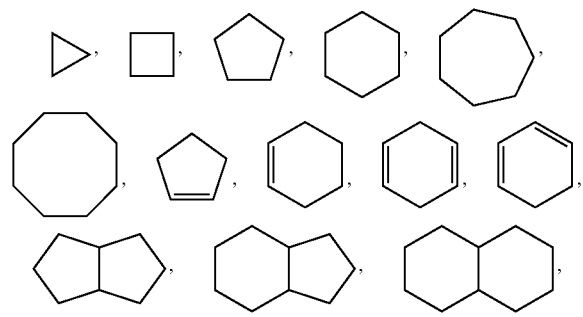

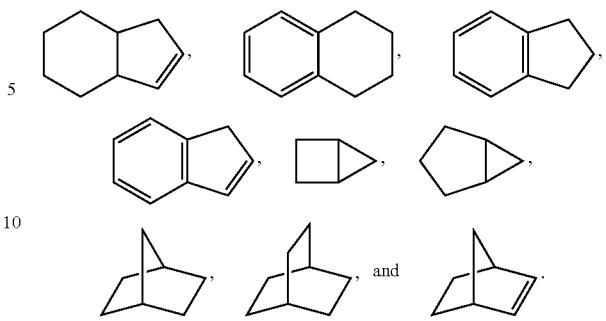

A "heterocycloalkyl" refers to a monocyclic ring structure that is saturated or partially saturated and has from 4 to 7 ring atoms per ring structure selected from carbon atoms and up to two heteroatoms selected from nitrogen, oxygen, and sulfur. The ring structure may optionally contain up to two oxo groups on sulfur ring members. Illustrative entities, in the form of properly bonded moieties, include:

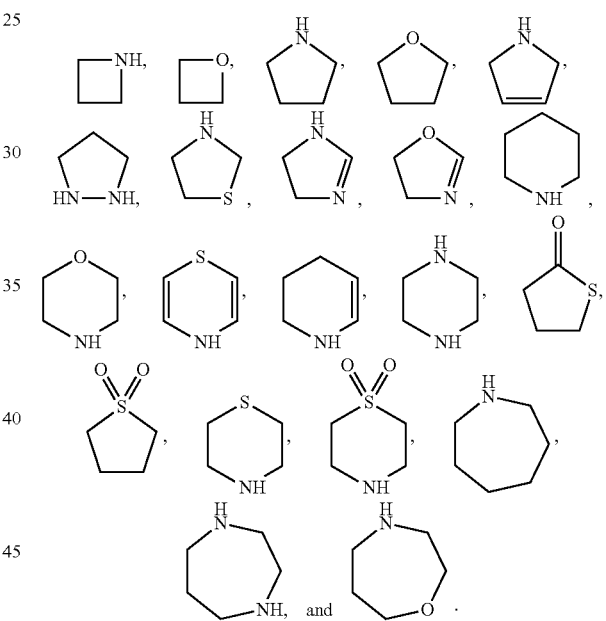

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

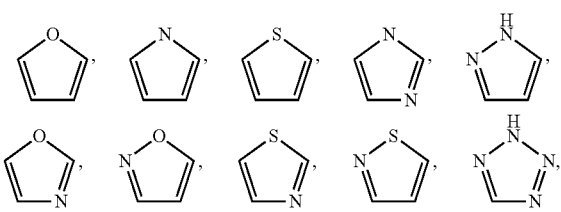

-continued

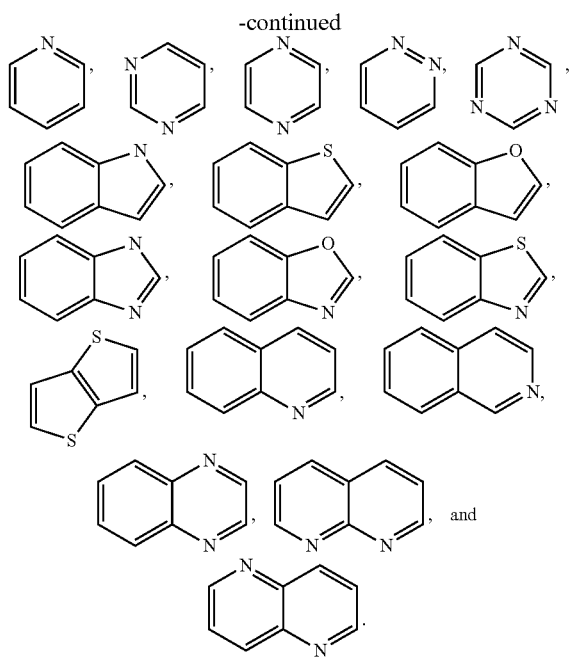

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}O$, $^{17}O$ $^{31}P$, $^{32}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is S$_4$; S$^1_{example}$ is S$_2$ and S$^2_{example}$ is S$_3$; S$^1_{example}$ is S$_2$ and S$^2_{example}$ is S$_4$; and equivalents of each one of such choices. The shorter terminology "S$^1_{example}$ is one of S$_1$ and S$_2$, and S$^2_{example}$ is one of S$_3$ and S$_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as R$^1$, R$^2$, A, X$^4$, X$^5$, X$^6$, X$^7$, R$^a$, R$^b$, R$^c$, R$^d$, R$^e$, R$^f$, R$^g$, R$^h$, R$^i$, R$^j$, R$^k$, R$^l$, R$^m$, and R$^o$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent S$_{example}$ is one of S$_1$, S$_2$, and S$_3$, this listing refers to embodiments of this invention for which S$_{example}$ is S$_1$; S$_{example}$ is S$_2$; S$_{example}$ is S$_3$; S$_{example}$ is one of S$_1$ and S$_2$; S$_{example}$ is one of S$_1$ and S$_3$; S$_{example}$ is one of S$_2$ and S$_3$; S$_{example}$ is one of S$_1$, S$_2$ and S$_3$; and S$_{example}$ is any equivalent of each one of these choices. The shorter terminology "S$_{example}$ is one of S$_1$, S$_2$, and S$_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as as R$^1$, R$^2$, A, X$^4$, X$^5$, X$^6$, X$^7$, R$^a$, R$^b$, R$^c$, R$^d$, R$^e$, R$^f$, R$^g$, R$^h$, R$^i$, R$^j$, R$^k$, R$^l$, R$^m$, and R$^o$, and any other generic substituent symbol used herein.

The nomenclature "C$_{1-j}$" with j>i, when applied herein to a class of substituents, is meant to refer to embodiments of this invention for which each and every one of the number of carbon members, from i to j including i and j, is independently realized. By way of example, the term C$_{1-3}$ refers independently to embodiments that have one carbon member (C$_1$), embodiments that have two carbon members (C$_2$), and embodiments that have three carbon members (C$_3$).

The term C$_{n-m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

In certain embodiments of Formula (I), m is 1 and n is 3. In other embodiments, m is 2 and n is 2. In still other embodiments, m is 3 and n is 1. In still other embodiments, m is 1 and n is 2. In still other embodiments, m is 2 and n is 1.

In some embodiments, R$^1$ is hydrogen, methyl, ethyl, isopropyl, butyl, or benzyl. In other embodiments, R$^1$ is hydrogen or methyl.

In some embodiments, R$^2$ and R$^3$ are each independently hydrogen, methyl, ethyl, isopropyl, or benzyl. In other embodiments, R$^2$ and R$^3$ are both ethyl.

In some embodiments, R$^2$ and R$^3$ taken together with the nitrogen to which they are attached form pyrrolidine, piperidine, azepane, morpholine, or 1,1-dioxo-1λ$^6$-thiomorpholine, unsubstituted or substituted with one or two substitutents selected from —C$_{1-4}$alkyl, —OH, and halo. In other embodiments, R$^2$ and R$^3$ taken together with the nitrogen to which they are attached form pyrrolidin-1-yl, 2-methylpyrrolidin-1-yl, piperidinyl, 2-methylpiperidin-1-yl, 2,6-dimethylpiperidin-1-yl, 4-fluoropiperidin-1-yl, 4,4-difluoropiperidin-1-yl, azepan-1-yl, morpholin-4-yl, 3-methylmorpholin-4-yl, or 1,1-dioxo-1λ$^6$-thiomorpholin-4-yl.

In some embodiments, Ar is phenyl, unsubstituted or substituted with one or two R$^i$ substituents. In other embodiments, Ar is a monocyclic heteroaryl ring, unsubstituted or substituted with one or two R$^i$ substituents. In other embodiments, Ar is a bicyclic heteroaryl ring, unsubstituted or substituted with one or two R$^i$ substituents. In other embodiments, each R$^i$ substituent is selected from the group consisting of fluoro, methyl, isopropyl, methoxy, cyano, chloro, trifluoromethoxy; or two R$^i$ substituents taken together form —OCH$_2$O—. In other embodiments, Ar is 4-fluorophenyl, 4-methylphenyl, 4-methoxyphenyl, 4-cyanophenyl, or 4-chlorophenyl. In other embodiments, Ar is pyridyl or thiophenyl. In other embodiments, Ar is Ar is quinolinyl or benzofuranyl.

In certain preferred embodiments, the compound of Formula (I) is selected from the group consisting of:

| Ex. | Chemical Name |
| --- | --- |
| 1 | Diethyl-[4-(4-fluoro-phenyl)-6,7,8,9-tetrahydro-5H-pyrimido[4,5-c]azepin-2-yl]-amine; |
| 2 | Diethyl-[4-(4-fluoro-phenyl)-6,7,8,9-tetrahydro-5H-pyrimido[4,5-c]azepin-2-yl]-amine; |
| 3 | Diethyl-[4-(4-methoxy-phenyl)-6,7,8,9-tetrahydro-5H-pyrimido[4,5-c]azepin-2-yl]-amine; |
| 4 | 4-(2-Diethylamino-6,7,8,9-tetrahydro-5H-pyrimido[4,5-c]azepin-4-yl)-benzonitrile; |
| 5 | 4-(4-Methoxy-phenyl)-2-(2-methyl-piperidin-1-yl)-6,7,8,9-tetrahydro-5H-pyrimido[4,5-c]azepine; |
| 6 | 4-(4-Fluoro-phenyl)-2-(2-methyl-piperidin-1-yl)-6,7,8,9-tetrahydro-5H-pyrimido[4,5-c]azepine; |
| 7 | 4-[2-(2-Methyl-piperidin-1-yl)-6,7,8,9-tetrahydro-5H-pyrimido[4,5-c]azepin-4-yl]-benzonitrile; |
| 8 | 2-(2-Methyl-piperidin-1-yl)-4-p-tolyl-6,7,8,9-tetrahydro-5H-pyrimido[4,5-c]azepine; |
| 9 | Diethyl-[4-(4-fluoro-phenyl)-6,7,8,9-tetrahydro-5H-pyrimido[4,5-d]azepin-2-yl]-amine; |
| 10 | Diethyl-(4-pyridin-4-yl-6,7,8,9-tetrahydro-5H-pyrimido[4,5-d]azepin-2-yl)-amine; |
| 11 | Diethyl-(4-p-tolyl-6,7,8,9-tetrahydro-5H-pyrimido[4,5-d]azepin-2-yl)-amine; |

-continued

| Ex. | Chemical Name |
|---|---|
| 12 | Diethyl-(4-thiophen-3-yl-6,7,8,9-tetrahydro-5H-pyrimido[4,5-d]azepin-2-yl)-amine; |
| 13 | Diethyl-[4-(4-methoxy-phenyl)-6,7,8,9-tetrahydro-5H-pyrimido[4,5-d]azepin-2-yl]-amine; |
| 14 | 4-(2-Diethylamino-6,7,8,9-tetrahydro-5H-pyrimido[4,5-d]azepin-4-yl)-benzonitrile; |
| 15 | Diethyl-[4-(4-fluoro-phenyl)-6,7,8,9-tetrahydro-5H-1,3,6-triaza-benzocyclohepten-2-yl]-amine; |
| 16 | Diethyl-(4-p-tolyl-6,7,8,9-tetrahydro-5H-1,3,6-triaza-benzocyclohepten-2-yl)-amine; |
| 17 | Diethyl-[4-(4-methoxy-phenyl)-6,7,8,9-tetrahydro-5H-1,3,6-triaza-benzocyclohepten-2-yl]-amine; |
| 18 | 4-(2-Diethylamino-6,7,8,9-tetrahydro-5H-1,3,6-triaza-benzocyclohepten-4-yl)-benzonitrile; |
| 19 | 2-Piperidin-1-yl-4-p-tolyl-6,7,8,9-tetrahydro-5H-1,3,6-triaza-benzocycloheptene; |
| 20 | 4-(4-Fluoro-phenyl)-2-piperidin-1-yl-6,7,8,9-tetrahydro-5H-1,3,6-triaza-benzocycloheptene; |
| 21 | 4-(4-Methoxy-phenyl)-2-piperidin-1-yl-6,7,8,9-tetrahydro-5H-1,3,6-triaza-benzocycloheptene; |
| 22 | 4-(2-Piperidin-1-yl-6,7,8,9-tetrahydro-5H-1,3,6-triaza-benzocyclohepten-4-yl)-benzonitrile; |
| 23 | [7-Benzyl-4-(4-fluoro-phenyl)-5,6,7,8-tetrahydro-pyrido[3,4-d]pyrimidin-2-yl]-diethyl-amine; |
| 24 | Diethyl-[4-(4-fluoro-phenyl)-5,6,7,8-tetrahydro-pyrido[3,4-d]pyrimidin-2-yl]-amine; |
| 25 | (7-Benzyl-4-p-tolyl-5,6,7,8-tetrahydro-pyrido[3,4-d]pyrimidin-2-yl)-diethyl-amine; |
| 26 | Diethyl-(4-p-tolyl-5,6,7,8-tetrahydro-pyrido[3,4-d]pyrimidin-2-yl)-amine; |
| 27 | [7-Benzyl-4-(4-methoxy-phenyl)-5,6,7,8-tetrahydro-pyrido[3,4-d]pyrimidin-2-yl]-diethyl-amine; |
| 28 | Diethyl-[4-(4-methoxy-phenyl)-5,6,7,8-tetrahydro-pyrido[3,4-d]pyrimidin-2-yl]-amine; |
| 29 | 4-(7-Benzyl-2-diethylamino-5,6,7,8-tetrahydro-pyrido[3,4-d]pyrimidin-4-yl)-benzonitrile; |
| 30 | 4-(2-Diethylamino-5,6,7,8-tetrahydro-pyrido[3,4-d]pyrimidin-4-yl)-benzonitrile; |
| 31 | 2-Azepan-1-yl-7-benzyl-4-(4-fluoro-phenyl)-5,6,7,8-tetrahydro-pyrido[3,4-d]pyrimidine; |
| 32 | 2-Azepan-1-yl-4-(4-fluoro-phenyl)-5,6,7,8-tetrahydro-pyrido[3,4-d]pyrimidine; |
| 33 | 2-Azepan-1-yl-7-benzyl-4-p-tolyl-5,6,7,8-tetrahydro-pyrido[3,4-d]pyrimidine; |
| 34 | 2-Azepan-1-yl-4-p-tolyl-5,6,7,8-tetrahydro-pyrido[3,4-d]pyrimidine; |
| 35 | 2-Azepan-1-yl-7-benzyl-4-(4-methoxy-phenyl)-5,6,7,8-tetrahydro-pyrido[3,4-d]pyrimidine; |
| 36 | 2-Azepan-1-yl-4-(4-methoxy-phenyl)-5,6,7,8-tetrahydro-pyrido[3,4-d]pyrimidine; |
| 37 | 4-(2-Azepan-1-yl-7-benzyl-5,6,7,8-tetrahydro-pyrido[3,4-d]pyrimidin-4-yl)-benzonitrile; |
| 38 | 4-(4-Fluoro-phenyl)-2-(2-methyl-pyrrolidin-1-yl)-5,6,7,8-tetrahydro-pyrido[4,3-d]pyrimidine; |
| 39 | [4-(4-Fluoro-phenyl)-5,6,7,8-tetrahydro-pyrido[4,3-d]pyrimidin-2-yl]-dimethyl-amine; |
| 40 | Diethyl-[4-(4-fluoro-phenyl)-5,6,7,8-tetrahydro-pyrido[4,3-d]pyrimidin-2-yl]-amine; |
| 41 | 4-(4-Fluoro-phenyl)-2-pyrrolidin-1-yl-5,6,7,8-tetrahydro-pyrido[4,3-d]pyrimidine; |
| 42 | 4-(4-Fluoro-phenyl)-2-morpholin-4-yl-5,6,7,8-tetrahydro-pyrido[4,3-d]pyrimidine; |
| 43 | [4-(4-Fluoro-phenyl)-5,6,7,8-tetrahydro-pyrido[4,3-d]pyrimidin-2-yl]-diisopropyl-amine; |
| 44 | Ethyl-[4-(4-fluoro-phenyl)-5,6,7,8-tetrahydro-pyrido[4,3-d]pyrimidin-2-yl]-methyl-amine; |
| 45 | 4-(4-Fluoro-phenyl)-2-(3-methyl-morpholin-4-yl)-5,6,7,8-tetrahydro-pyrido[4,3-d]pyrimidine; |
| 46 | [4-(4-Chloro-phenyl)-5,6,7,8-tetrahydro-pyrido[4,3-d]pyrimidin-2-yl]-diethyl-amine; |
| 47 | 2-Pyrrolidin-1-yl-4-p-tolyl-5,6,7,8-tetrahydro-pyrido[4,3-d]pyrimidine; |
| 48 | Ethyl-(4-p-tolyl-5,6,7,8-tetrahydro-pyrido[4,3-d]pyrimidin-2-yl)-amine; |
| 49 | 2-Morpholin-4-yl-4-p-tolyl-5,6,7,8-tetrahydro-pyrido[4,3-d]pyrimidine; |
| 50 | 2-Piperidin-1-yl-4-p-tolyl-5,6,7,8-tetrahydro-pyrido[4,3-d]pyrimidine; |
| 51 | Benzyl-(4-p-tolyl-5,6,7,8-tetrahydro-pyrido[4,3-d]pyrimidin-2-yl)-amine; |
| 52 | 6-Methyl-2-pyrrolidin-1-yl-4-p-tolyl-5,6,7,8-tetrahydro-pyrido[4,3-d]pyrimidine; |

-continued

| Ex. | Chemical Name |
|---|---|
| 53 | 4-(4-Chloro-phenyl)-2-(2-methyl-pyrrolidin-1-yl)-6,7,8,9-tetrahydro-5H-1,3,6-triaza-benzocycloheptene; |
| 54 | 4-(4-Chloro-phenyl)-2-(2-methyl-pyrrolidin-1-yl)-6,7,8,9-tetrahydro-5H-pyrimido[4,5-d]azepine; |
| 55 | Benzyl-[4-(4-chloro-phenyl)-6,7,8,9-tetrahydro-5H-1,3,6-triaza-benzocyclohepten-2-yl]-amine; |
| 56 | Benzyl-[4-(4-chloro-phenyl)-6,7,8,9-tetrahydro-5H-pyrimido[4,5-d]azepin-2-yl]-amine; |
| 57 | 4-(4-Chloro-phenyl)-2-morpholin-4-yl-6,7,8,9-tetrahydro-5H-1,3,6-triaza-benzocycloheptene; |
| 58 | 4-(4-Chloro-phenyl)-2-morpholin-4-yl-6,7,8,9-tetrahydro-5H-pyrimido[4,5-d]azepine; |
| 59 | [4-(4-Chloro-phenyl)-6,7,8,9-tetrahydro-5H-1,3,6-triaza-benzocyclohepten-2-yl]-diethyl-amine; |
| 60 | [4-(4-Chloro-phenyl)-6,7,8,9-tetrahydro-5H-pyrimido[4,5-d]azepin-2-yl]-diethyl-amine; |
| 61 | Dimethyl-(4-p-tolyl-5,6,7,8-tetrahydro-pyrido[4,3-d]pyrimidin-2-yl)-amine; |
| 64 | 2-(1,1-Dioxo-1$\lambda^6$-thiomorpholin-4-yl)-4-p-tolyl-6,7,8,9-tetrahydro-5H-pyrimido[4,5-d]azepine; |
| 65 | 2-(1,1-Dioxo-1$\lambda^6$-thiomorpholin-4-yl)-7-methyl-4-p-tolyl-6,7,8,9-tetrahydro-5H-pyrimido[4,5-d]azepine; |
| 66 | 4-(3-chloro-4-methoxyphenyl)-6,7,8,9-tetrahydro-2-(2-methyl-1-pyrrolidinyl)-5H-pyrimido[4,5-d]azepine; |
| 67 | 4-(3,4-dichlorophenyl)-2-(4-fluoro-1-piperidinyl)-6,7,8,9-tetrahydro-5H-pyrimido[4,5-d]azepine; |
| 68 | 4-(4-chlorophenyl)-2-(4-fluoro-1-piperidinyl)-6,7,8,9-tetrahydro-5H-pyrimido[4,5-d]azepine; |
| 69 | 2-(4-fluoro-1-piperidinyl)-6,7,8,9-tetrahydro-4-(4-methylphenyl)-5H-pyrimido[4,5-d]azepine; |
| 70 | 4-(4-chlorophenyl)-2-[(2R,6S)-2,6-dimethyl-1-piperidinyl]-6,7,8,9-tetrahydro-5H-pyrimido[4,5-d]azepine; |
| 71 | 2-[(2R,6S)-2,6-dimethyl-1-piperidinyl]-6,7,8,9-tetrahydro-4-(4-methylphenyl)-5H-pyrimido[4,5-d]azepine; |
| 72 | 6,7,8,9-tetrahydro-4-(4-methylphenyl)-2-(2-methyl-1-pyrrolidinyl)-5H-pyrimido[4,5-d]azepine; |
| 73 | 4-(3,4-dichlorophenyl)-2-[(2R,6S)-2,6-dimethyl-1-piperidinyl]-6,7,8,9-tetrahydro-5H-pyrimido[4,5-d]azepine; |
| 74 | 4-(4-chlorophenyl)-6,7,8,9-tetrahydro-2-(1-piperidinyl)-5H-pyrimido[4,5-d]azepine; |
| 75 | 4-(3-chloro-4-methylphenyl)-6,7,8,9-tetrahydro-2-(1-piperidinyl)-5H-pyrimido[4,5-d]azepine; |
| 76 | 4-(3-chloro-4-methylphenyl)-2-(4-fluoro-1-piperidinyl)-6,7,8,9-tetrahydro-5H-pyrimido[4,5-d]azepine; |
| 77 | 4-(3-chloro-4-methylphenyl)-6,7,8,9-tetrahydro-2-(2-methyl-1-pyrrolidinyl)-5H-pyrimido[4,5-d]azepine; |
| 78 | 6,7,8,9-tetrahydro-4-(4-methylphenyl)-2-(1-piperidinyl)-5H-pyrimido[4,5-d]azepine; |
| 79 | 4-(3-chloro-4-methylphenyl)-2-[(2R,6S)-2,6-dimethyl-1-piperidinyl]-6,7,8,9-tetrahydro-5H-pyrimido[4,5-d]azepine; |
| 80 | 6,7,8,9-tetrahydro-4-(4-methoxyphenyl)-2-(2-methyl-1-pyrrolidinyl)-5H-pyrimido[4,5-d]azepine; |
| 81 | 2-(4-fluoro-1-piperidinyl)-6,7,8,9-tetrahydro-4-(4-methoxyphenyl)-5H-pyrimido[4,5-d]azepine; |
| 82 | 2-[(2R,6S)-2,6-dimethyl-1-piperidinyl]-6,7,8,9-tetrahydro-4-(4-methoxyphenyl)-5H-pyrimido[4,5-d]azepine; |
| 83 | 4-(3,4-difluorophenyl)-2-[(2R,6S)-2,6-dimethyl-1-piperidinyl]-6,7,8,9-tetrahydro-5H-pyrimido[4,5-d]azepine; |
| 84 | 4-(4-chloro-3-fluorophenyl)-2-[(2R,6S)-2,6-dimethyl-1-piperidinyl]-6,7,8,9-tetrahydro-5H-pyrimido[4,5-d]azepine; |
| 85 | 2-[(2R,6S)-2,6-dimethyl-1-piperidinyl]-4-(3-fluoro-4-methylphenyl)-6,7,8,9-tetrahydro-5H-pyrimido[4,5-d]azepine; |
| 86 | 2-[(2R,6S)-2,6-dimethyl-1-piperidinyl]-6,7,8,9-tetrahydro-4-(6-methyl-3-pyridinyl)-5H-pyrimido[4,5-d]azepine; |
| 87 | 4-(2,3-dihydro-1,4-benzodioxin-6-yl)-2-[(2R,6S)-2,6-dimethyl-1-piperidinyl]-6,7,8,9-tetrahydro-5H-pyrimido[4,5-d]azepine; |
| 88 | 2-[(2R,6S)-2,6-dimethyl-1-piperidinyl]-6,7,8,9-tetrahydro-4-(3-quinolinyl)-5H-pyrimido[4,5-d]azepine; |
| 89 | 2-[(2R,6S)-2,6-dimethyl-1-piperidinyl]-4-(3-fluoro-4-methoxyphenyl)-6,7,8,9-tetrahydro-5H-pyrimido[4,5-d]azepine; |
| 90 | 2-[(2R,6S)-2,6-dimethyl-1-piperidinyl]-6,7,8,9-tetrahydro-4-[4-(trifluoromethoxy)phenyl]-5H-pyrimido[4,5-d]azepine; |
| 91 | 2-[(2R,6S)-2,6-dimethyl-1-piperidinyl]-6,7,8,9-tetrahydro-4-[4-(1-methylethyl)phenyl]-5H-pyrimido[4,5-d]azepine; |
| 92 | 4-(3-Chloro-4-methyl-phenyl)-2-(1,1-dioxo-1$\lambda^6$-thiomorpholin-4-yl)-6,7,8,9-tetrahydro-5H-pyrimido[4,5-d]azepine; |

-continued

| Ex. | Chemical Name |
|---|---|
| 93 | 4-(3-chloro-4-methylphenyl)-6,7,8,9-tetrahydro-2-[(3S)-3-methyl-4-morpholinyl]-5H-pyrimido[4,5-d]azepine; |
| 94 | 6,7,8,9-tetrahydro-2-[(3S)-3-methyl-4-morpholinyl]-4-(4-methylphenyl)-5H-pyrimido[4,5-d]azepine; |
| 95 | 6,7,8,9-tetrahydro-2-[(3S)-3-methyl-4-morpholinyl]-4-(3-quinolinyl)-5H-pyrimido[4,5-d]azepine; |
| 96 | 4-(4-chlorophenyl)-6,7,8,9-tetrahydro-2-[(3S)-3-methyl-4-morpholinyl]-5H-pyrimido[4,5-d]azepine; |
| 97 | 4-(3-fluoro-4-methylphenyl)-6,7,8,9-tetrahydro-2-[(3S)-3-methyl-4-morpholinyl]-5H-pyrimido[4,5-d]azepine; |
| 98 | 4-(2-benzofuranyl)-6,7,8,9-tetrahydro-2-[(3S)-3-methyl-4-morpholinyl]-5H-pyrimido[4,5-d]azepine; |
| 99 | 6,7,8,9-tetrahydro-2-[(3R)-3-methyl-4-morpholinyl]-4-(3-quinolinyl)-5H-pyrimido[4,5-d]azepine; |
| 100 | 6,7,8,9-tetrahydro-2-[(3R)-3-methyl-4-morpholinyl]-4-(4-methylphenyl)-5H-pyrimido[4,5-d]azepine; |
| 101 | 2-(1,1-Dioxo-1$\lambda^6$-thiomorpholin-4-yl)-4-(4-isopropyl-phenyl)-6,7,8,9-tetrahydro-5H-pyrimido[4,5-d]azepine; |
| 102 | 2-Morpholin-4-yl-4-quinolin-3-yl-6,7,8,9-tetrahydro-5H-pyrimido[4,5-d]azepine; and |
| 103 | 2-(4,4-difluoro-1-piperidinyl)-6,7,8,9-tetrahydro-4-(3-quinolinyl)-5H-pyrimido[4,5-d]azepine; | and pharmaceutically acceptable salts thereof.

The invention includes also pharmaceutically acceptable salts of the compounds of Formula (I), preferably of those described above and of the specific compounds exemplified herein, and methods of treatment using such salts.

A "pharmaceutically acceptable salt" is intended to mean a salt of a free acid or base of a compound represented by Formula (I), that is non-toxic, biologically tolerable, or otherwise biologically suitable for administration to the subject. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenyl butyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Representative pharmaceutically acceptable amides of the invention include those derived from ammonia, primary $C_{1-6}$ alkyl amines and secondary di($C_{1-6}$alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$alkyl primary amines, and di($C_{1-2}$alkyl) amines. Representative pharmaceutically acceptable esters of the invention include $C_{1-7}$alkyl, $C_{5-7}$cycloalkyl, phenyl, and phenyl($C_{1-6}$)alkyl esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med. Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I), which may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J Med. Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites of the present invention are useful as serotonin receptor modulators in the methods of the invention. As such modulators, the compounds may act as antagonists, agonists, or inverse agonists. "Modulators" include both inhibitors and activators, where "inhibitors" refer to compounds that decrease, prevent, inactivate, desensitize or down-regulate serotonin receptor expression or activity, and "activators" are compounds that increase, activate, facilitate, sensitize, or up-regulate serotonin receptor expression or activity.

The term "treat" or "treating" as used herein is intended to refer to administration of an active agent or composition of the invention to a subject for the purpose of effecting a therapeutic or prophylactic benefit through modulation of serotonin receptor activity. Treating includes reversing, ameliorating, alleviating, inhibiting the progress of, lessening the severity of, or preventing a disease, disorder, or condition, or one or more symptoms of such disease, disorder or condition mediated through modulation of serotonin receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by serotonin receptor activity, such as: sleep disorders (including insomnia), depression/anxiety, generalized anxiety disorder, schizophrenia, bipolar disorders, cognitive disorders, mild cognitive impairment, Alzheimer's disease, Parkinson's disease, psychotic disorders, phobic disorders, obsessive-compulsive disorder, mood disorders, post-traumatic stress and other stress-related disorders, migraine, pain, eating disorders, obesity, sexual dysfunction, metabolic disturbances, hormonal imbalance, hot flushes associated with menopause, alcohol abuse, drug abuse, addictive disorders including drug addiction and alcohol addiction, nausea, inflammation, centrally mediated hypertension, sleep/wake disturbances, jetlag, and circadian rhythm abnormalities. The compounds may also be used in the treatment and prevention of hypotension, peripheral vascular disorders, cardiovascular shock, renal disorders, gastric motility, diarrhea, spastic colon, irritable bowel disorders, ischemias, septic shock, urinary incontinence, and other disorders related to the gastrointestinal and vascular systems. In addition, compounds of the present invention may be used in methods for treating or preventing a range of ocular disorders including glaucoma, optic neuritis, diabetic retinopathy, retinal edema, and age-related macular degeneration. Symptoms or disease states are intended to be included within the scope of "medical conditions, disorders, or diseases."

As 5-$HT_1$ modulators, compounds of the present invention are particularly useful in methods for treating or preventing depression/anxiety, sleep/wake disturbances, jetlag, migraine, urinary incontinence, gastric motility, and irritable bowel disorders.

As 5-$HT_2$ modulators, compounds of the present invention are useful in methods for treating or preventing depression/anxiety, generalized anxiety disorder, schizophrenia, bipolar disorders, psychotic disorders, obsessive-compulsive disorder, mood disorders, post-traumatic stress disorders, sleep disturbances, sexual dysfunction, hot flushes associated with menopause, eating disorders, migraine, addictive disorders, and peripheral vascular disorders.

As 5-$HT_6$ modulators, compounds of the present invention are useful in methods for treating or preventing schizophrenia, cognitive disorders, mild cognitive impairment, Alzheimer's disease, and Parkinson's disease.

Particularly, as serotonin receptor modulators, the compounds of the present invention are useful in the treatment or prevention of depression, anxiety, sleep disorders, and circadian rhythm abnormalities.

In treatment methods according to the invention, an effective amount of at least one compound according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. In an exemplary embodiment, additional active ingredients are those that are known or discovered to be effective in the treatment of conditions, disorders, or diseases mediated by serotonin receptors or that are active against another target associated with the particular condition, disorder, or disease. Suitable examples include: $H_1$ receptor antagonists, $H_2$ receptor antagonists, $H_3$ receptor antagonists, topiramate (TOPAMAX™), and neurotransmitter modulators such as norepinephrine reuptake inhibitors (NRIs), selective serotonin reuptake inhibitors (SSRIs), noradrenergic reuptake inhibitors, non-selective serotonin re-uptake inhibitors (NSSRIs), acetylcholinesterase inhibitors (such as tetrahydroaminoacridine, Donepezil (ARICEPT™), Rivastigmine, or Galantamine (REMINYL™)), modafinil, anti-psychotics, sedatives, monoamine oxidase inhibitors (MAOs), and tricyclic antidepressants (TCAs). The combination may serve to increase efficacy (e.g., by including in the combination a compound potentiating the potency or effectiveness of a compound according to the invention), decrease one or more side effects, or decrease the required dose of the compound according to the invention. In preferred embodiments, the combination method employs doses additional active ingredients in the range of about 20 to 300 mg per dose.

The compounds of the invention are used, alone or in combination with one or more other active ingredients, to formulate pharmaceutical compositions of the invention. A pharmaceutical composition of the invention comprises: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a compound of the invention and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the compounds of the invention may be prepared using suitable pharmaceutical excipients and compounding techniques now or later known or available to those skilled in the art. The compositions may be administered in the inventive methods by oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and diglycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compounds of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent.

| Table of Acronyms | |
|---|---|
| Term | Acronym |
| Tetrahydrofuran | THF |
| N,N-Dimethylformamide | DMF |
| N,N-Dimethylacetamide | DMA |
| Dimethyl sulfoxide | DMSO |
| tert-Butylcarbamoyl | Boc |
| High-pressure liquid chromatography | HPLC |
| Thin layer chromatography | TLC |
| N,N-Diisopropylethylamine | DIEA |
| 1,2-Dichloroethane | DCE |
| Ethylene glycol dimethyl ether | DME |
| Acetyl | Ac |
| Diisobutylaluminum hydride | DIBAL-H |
| Ethyl acetate | EtOAc |
| Trifluoroacetic acid | TFA |
| Methanesulfonyl chloride | MsCl |

The 2-aminopyrimidine compounds of Formula (I) are accessible by a number of reaction schemes. Persons skilled in the art will recognize that certain compounds are more advantageously produced by one scheme as compared to the other. In addition to the Schemes shown below, alternative methods may be used to prepare compounds of Formula (I). Such methods are described in U.S. patent application Ser. No. 11/460,294 (Dvorak et al.), which is hereby incorporated by reference.

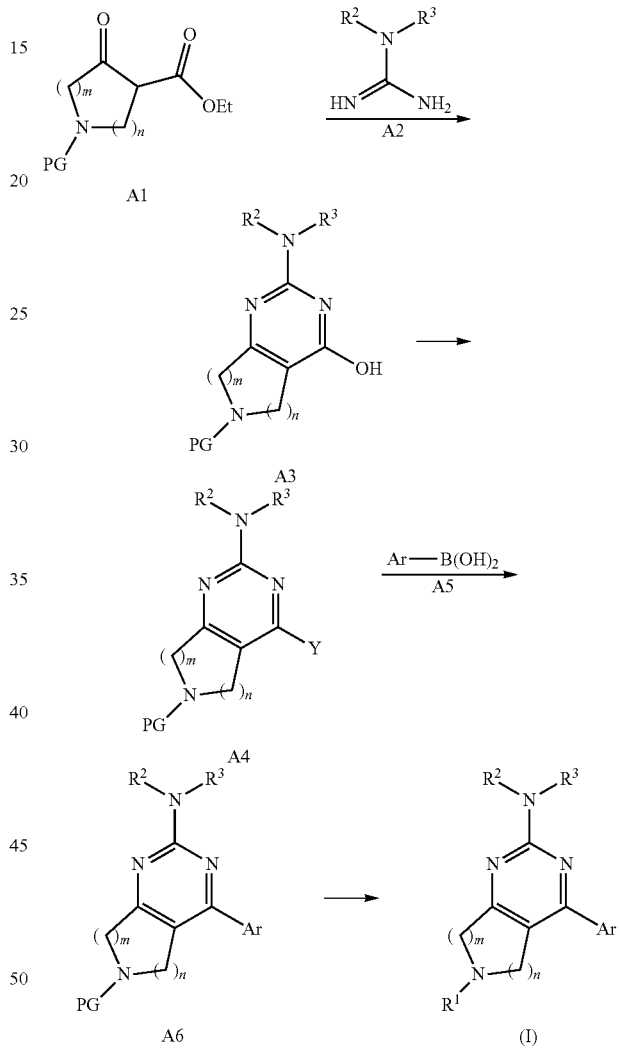

Referring to Scheme A, compounds of Formula (I) are prepared from beta-ketoesters A1, which are commercially available or are prepared by methods known in the art. The substituent "PG" is a suitable amine protecting group, such as a benzyl, benzoyl, or carbamoyl group. Preferred protecting groups include t-butyl carbamate (Boc) or benzyl groups. Reaction of beta-ketoesters A1 with amidines A2 (commercially available or prepared by methods known in the art) in the presence of a suitable base, such as NaOEt, NaOtBu, KOtBu, $K_2CO_3$, or $Et_3N$, in a solvent such as EtOH, tBuOH, t-amyl alcohol, or acetonitrile gives hydroxy pyrimidines A3. (See also: Tetrahedron 1989, 45(20), 6511). Pyrimidines A3 are converted into precursors for transition metal-catalyzed cross-coupling reactions, such as Stille, Suzuki, Negishi or other such coupling reactions known to one skilled in the art. For example, treatment with POCl$_3$, PCl$_5$, PCl$_5$, PBr$_3$ or POBr$_3$ affords the corresponding halopyrimidines A4, where Y is bromide or chloride. Alternatively, pyrimidines A3 are treated with a triflating agent such as trifluoromethane-sulfonic anhydride or N-phenyl-bis(trifluoromethane-sulfonimide) in DCE, CH$_2$Cl$_2$, THF, or the like, in the presence of a base such as pyridine, Et$_3$N, DIEA, or KOtBu, to provide triflates A4 where Y is OTf. Coupling of halides or triflates A4 with aryl boronic acids A5, or their boronic ester analogs, in the presence of a catalyst such as Pd(PPh$_3$)$_4$, PdCl$_2$(PPh$_3$)$_2$, PdCl$_2$(Po-tol$_3$)$_2$, PdCl$_2$(dppe) or PdCl$_2$(dppf), in a solvent such as THF, 1,4-dioxane, DMA, DMF, DME, toluene, toluene/ethanol, or toluene/H$_2$O mixtures, in the presence of a base such as Na$_2$CO$_3$, K$_2$CO$_3$, Cs$_2$CO$_3$, K$_3$PO$_4$, KF, CsF, or KOAc, affords pyrimidines A6. Preferred catalysts are Pd(PPh$_3$)$_4$ and PdCl$_2$(dppf), with or without additives such as dppf and catalytic Bu$_4$NBr. Preferred conditions employ PdCl$_2$(dppf), catalytic dppf, and K$_3$PO$_4$ in 1,4-dioxane. The PG protecting group is then removed using generally accepted methods. More specifically, a group such as a t-butyl carbamate is removed with an acid such as trifluoroacetic acid or HCl, in a solvent such as CH$_2$Cl$_2$, dioxane, EtOH, or MeOH to afford compounds of Formula (I) where R$^1$ is H. Where PG is a benzyl group, compounds A6 are embodiments of Formula (I). Removal of the benzyl group according to standard methods, including hydrogenation in the presence of a palladium catalyst such as Pd/C, in a solvent such as EtOH, or through reaction with 1-chloroethylchloroformate in DCE, provides embodiments of Formula (I) where R$^1$ is H.

Compounds of Formula (I) where R$^1$ is H are converted into additional embodiments of Formula (I) using conventional synthetic methods. Exemplary protocols include, for example, reductive amination with a suitable aldehyde or ketone in the presence of a reducing agent such as NaBH$_4$, NaBH$_3$CN, NaBH(OAc)$_3$, or H$_{2(g)}$, in the presence of a catalyst, and in a solvent such as CH$_2$Cl$_2$, DCE, THF, EtOH, or MeOH. One skilled in the art will recognize that the addition of an acid such as ZnCl$_2$, AcOH, Ti(O-iPr)$_4$, trifluoroacetic acid, or HCl, may be required. Alternatively, reaction conditions include treatment of compounds of Formula (I), where R$^1$ is H, with an alkylating agent, such as an alkyl chloride, bromide, iodide, mesylate or tosylate, in a solvent such as DMF, DMA, THF, or EtOH, and in the presence of a base such as NaHCO$_3$, Na$_2$CO$_3$, K$_2$CO$_3$ or Cs$_2$CO$_3$.

SCHEME B

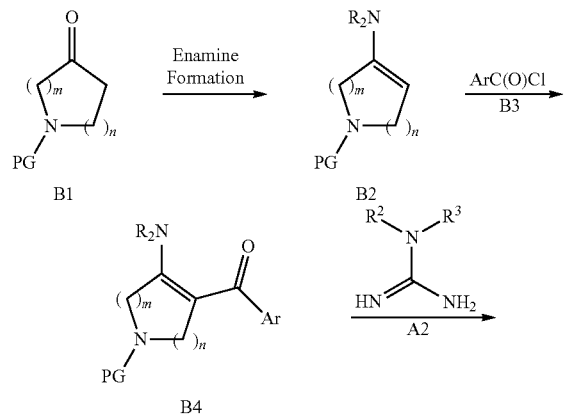

Pyrimidines A6 are also available as shown in Scheme B. Ketones B1 are commercially available or are prepared using methods known to one skilled in the art. The protecting group PG is preferably an acyl group or carbamoyl group (such as a Boc group). Conversion to enamines B2 is accomplished by reaction with a secondary amine R$_2$NH (such as iPr$_2$NH, morpholine, or piperidine) under standard water removal conditions. Preferably, the reaction is done with piperidine as the secondary amine, and using a Dean Stark trap, with a catalyst such as p-toluenesulfonic acid, in a solvent such as toluene. Elevated temperatures are preferred. Enamines B2 are transformed into enamides B4 by reaction with acyl chlorides B3, in the presence of a suitable base such as Et$_3$N, in a solvent such as CH$_2$Cl$_2$. (See also: Breitenbucher, et al. PCT Intl. Appl. WO02/014314). Condensation of enamides B4 with amidines A5 to form pyrimidines A6 is accomplished as described in Scheme A. Preferably, condensations are performed in the presence of Et$_3$N, in a solvent such as t-amyl alcohol, at temperatures between room temperature and reflux temperature of the solvent. Compounds A6 are themselves embodiments of Formula (I), or are converted into additional embodiments as described in Scheme A.

Those skilled in the art will recognize that several of the chemical transformations described above may be performed in a different order than that depicted in the above Schemes.

Compounds of Formula (I) may be converted to their corresponding salts using methods known to those skilled in the art. For example, an amine of Formula (I) is treated with TFA, HCl, maleic acid, or citric acid in a solvent such as Et$_2$O, CH$_2$Cl$_2$, THF, or MeOH to provide the corresponding salt form.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following examples are provided to further illustrate the invention and various preferred embodiments.

EXAMPLES

Chemistry

In preparing the compounds described in the examples below and obtaining the corresponding analytical data, the following experimental and analytical protocols were followed unless otherwise indicated.

Unless otherwise specified, reaction mixtures were magnetically stirred at room temperature (rt) under a $N_{2(g)}$ atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure.

Normal-phase flash column chromatography (FCC) was performed on silica gel ($SiO_2$) eluting with EtOAc/hexanes or 2 M $NH_3$/MeOH in $CH_2Cl_2$, unless otherwise noted.

Reversed-phase HPLC was performed on a Hewlett Packard HPLC Series 1100, with a Agilent ZORBAX® Bonus RP, 5 μm, 4.6×250 mm column. Detection was done at λ=230, 254 and/or 280 nm. The gradient was 1 to 99% acetonitrile/water (0.05% trifluoroacetic acid) over 20.0 min with a flow rate of 1 mL/min.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1H$ NMR data below is: chemical shift in ppm downfield of the tetramethylsilane reference for $CDCl_3$ (multiplicity, coupling constant J in Hz, integration). When MeOH-$d_4$ (3.31 ppm) or DMSO-$d_6$ (2.50 ppm) were utilized as NMR solvents residual protic solvent was utilized as the reference.

Chemical names were generated using ChemDraw Version 6.0.2 (CambridgeSoft, Cambridge, Mass.).

Example 1

Diethyl-[4-(4-fluoro-phenyl)-6,7,8,9-tetrahydro-5H-pyrimido[4,5-c]azepin-2-yl]-amine

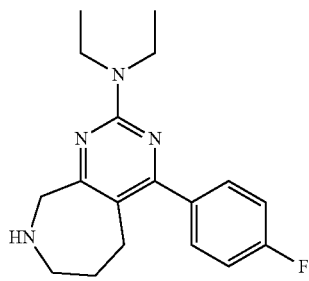

Step A: 3-Oxo-azepane-1,4-dicarboxylic acid 1-tert-butyl ester 4-ethyl ester and 4-oxo-azepane-1,3-dicarboxylic acid 1-tert-butyl ester 3-ethyl ester To a 0° C. solution of 3-oxo-piperidine-1-carboxylic acid tert-butyl ester (11.3 g, 56.7 mmol) in $Et_2O$ (170 mL) was added $BF_3 \cdot Et_2O$ (7.2 mL, 56.7 mmol) followed by ethyl diazoacetate (7.2 mL, 68.0 mmol) dropwise over 30 min. After an additional 1 h, satd. aq. $NaHCO_3$ was added and the solution was stirred for 1 h, then was extracted with $Et_2O$ (2×). The combined organic layers were washed with brine, dried, and concentrated. The resulting residue was purified by FCC to give 5.48 g (34%) of the title compound and 5.25 g (32%) of the more polar 4-oxo-azepane-1,3-dicarboxylic acid 1-tert-butyl ester 3-ethyl ester.

Step B: 2-Diethylamino-4-hydroxy-5,6,7,9-tetrahydro-pyrimido[4,5-c]azepine-8-carboxylic acid tert-butyl ester To a solution of 3-oxo-azepane-1,4-dicarboxylic acid 1-tert-butyl ester 4-ethyl ester (0.67 g, 2.3 mmol) in EtOH (10 mL) was added diethyl guanidinium trifluoroacetate (0.54 g, 2.3 mmol) and sodium ethoxide (21 wt % in EtOH, 2.3 mL). The reaction was heated at reflux for 16 h then cooled to room temperature (rt). The reaction mixture was diluted with $H_2O$ and extracted with $CH_2Cl_2$ (2×). The combined organic extracts were dried and concentrated. The resulting material was triturated with hexanes/$Et_2O$ (9:1) to give the title compound (0.334 mg, 43%) as a light brown solid. MS (ESI): mass calcd. for $C_{17}H_{28}N_4O_3$, 336.4; m/z found, 337.4 $[M+H]^+$. $^1H$ NMR ($CDCl_3$): 4.34-4.25 (m, 2H), 3.62-3.46 (m, 6H), 2.66-2.58 (m, 2H), 1.88-1.77 (m, 2H), 1.50-1.36 (m, 9H), 1.21-1.14 (m, 6H).

Step C: 2-Diethylamino-4-trifluoromethanesulfonyloxy-5,6,7,9-tetrahydro-pyrimido[4,5-c]azepine-8-carboxylic acid tert-butyl ester To a solution of 2-diethylamino-4-hydroxy-5,6,7,9-tetrahydro-pyrimido[4,5-c]azepine-8-carboxylic acid tert-butyl ester (0.256 g, 0.76 mmol) in $CH_2Cl_2$ (3 mL) at 0° C. was added $Et_3N$ (0.102 g, 0.140 mL, 1.0 mmol) followed by triflic anhydride (0.25 g, 0.15 mL, 0.9 mmol). After 1 h, the mixture was diluted with $H_2O$ and extracted with $CH_2Cl_2$ (2×). The combined organic layers were dried and concentrated. Purification by FCC provided the title compound (0.338 g, 95%) as a clear oil which solidified overtime. MS (ESI): mass calcd. for $C_{18}H_{27}F_3N_4O_5S$, 468.5; m/z found, 469.3 $[M+H]^+$. $^1H$ NMR ($CDCl_3$): 4.51-4.42 (m, 2H), 3.66-3.44 (m, 6H), 2.72-2.65 (m, 2H), 1.90-1.83 (m, 2H), 1.49-1.36 (m, 9H), 1.19-1.12 (m, 6H).

Step D: 2-Diethylamino-4-(4-fluoro-phenyl)-5,6,7,9-tetrahydro-pyrimido[4,5-c]azepine-8-carboxylic acid tert-butyl ester To 2-diethylamino-4-trifluoromethanesulfonyloxy-5,6,7,9-tetrahydro-pyrimido[4,5-c]azepine-8-carboxylic acid tert-butyl ester (0.071 g, 0.15 mmol) was added 4-fluoroboronic acid (0.032 g, 0.23 mmol), $K_3PO_4$ (0.047 g, 0.22 mmol), Pd(dppf)$Cl_2$ (0.007 g, 0.009 mmol), and dppf (0.006 g, 0.010 mmol). The flask was fitted with a reflux condenser, evacuated under vacuum and refilled with $N_2$. Dioxane (2 mL) was added and the mixture was heated at 100° C. for 3 h, then cooled to rt and diluted with $Et_2O$. The mixture was filtered through a small pad of $SiO_2$. The filtrate was concentrated and purified by FCC to provide the title compound (0.057 g, 92%) as a light yellow clear oil. MS (ESI): mass calcd. for $C_{23}H_{31}FN_4O_2$, 414.5; m/z found, 415.4 $[M+H]^+$. $^1H$ NMR ($CDCl_3$): 7.49-7.45 (dd, J=8.5, 5.6, 1H), 7.11 (t, J=8.7, 2H), 4.58-4.41 (m, 2H), 3.71-3.54 (m, 6H), 2.77-2.61 (m, 2H), 1.86-1.76 (m, 2H), 1.49-1.39 (m, 9H), 1.18 (t, J=6.9, 6H).

Step E: Diethyl-[4-(4-fluoro-phenyl)-6,7,8,9-tetrahydro-5H-pyrimido[4,5-c]azepin-2-yl]-amine To a solution of 2-diethylamino-4-(4-fluoro-phenyl)-5,6,7, 9-tetrahydro-pyrimido[4,5-c]azepine-8-carboxylic acid tert-butyl ester (0.058 g, 0.14 mmol) in EtOAc (1 mL) was added 4 M HCl in dioxane (2 mL). After 16 h, the mixture was concentrated, diluted with saturated (satd.) aqueous (aq.) NaHCO$_3$, and extracted with CH$_2$Cl$_2$. The combined organic layers were dried and concentrated. Purification by FCC (2 M NH$_3$ in MeOH/CH$_2$Cl$_2$) provided the title compound (>90%). HPLC: R$_t$=9.7 min. MS (ESI): mass calcd. for C$_{18}$H$_{23}$FN$_4$, 314.4; m/z found, 315.4 [M+H]$^+$. $^1$H NMR (CDCl$_3$): 7.47 (dd, J=8.7, 5.5, 2H), 7.11 (t, J=8.7, 2H), 3.96 (5, 2H), 3.64 (q, J=7.0, 4H), 3.21-3.18 (m, 1H), 2.80-2.76 (m, 2H), 1.93-1.86 (m, 2H), 1.71-1.67 (m, 1H), 1.17 (t, J=7.0, 6H).

Step F.

A solution of diethyl-[4-(4-fluoro-phenyl)-6,7,8,9-tetrahydro-5H-pyrimido[4,5-c]azepin-2-yl]-amine in EtOAc was treated with 1 M HCl in Et$_2$O. The resulting white solid was isolated after concentration and trituration with Et$_2$O to provide the title compound.

The compounds in Examples 2-8 were prepared using methods analogous to those described in Example 1, Steps A-E (free bases) or Steps A-F (hydrochloride salts).

Example 2

Diethyl-[4-(4-fluoro-phenyl)-6,7,8,9-tetrahydro-5H-pyrimido[4,5-c]azepin-2-yl]-amine

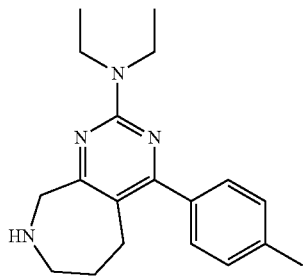 [SMILES: CCN(CC)c1nc2c(c(-c3ccc(C)cc3)n1)CCCNC2]

HPLC: R$_t$=10.0 min. MS (ESI): mass calcd. for C$_{19}$H$_{26}$N$_4$, 310.4; m/z found, 311.4 [M+H]$^+$. $^1$H NMR (CDCl$_3$): 7.39 (d, J=8.1, 2H), 7.23 (d, J=7.9, 2H), 3.96 (s, 2H), 3.64 (q, J=7.0, 4H), 3.21-3.17 (m, 2H), 2.81-2.79 (m, 2H), 2.40 (s, 3H), 1.71-1.66 (m, 2H), 1.17 (t, J=7.0, 6H).

Example 3

Diethyl-[4-(4-methoxy-phenyl)-6,7,8,9-tetrahydro-5H-pyrimido[4,5-c]azepin-2-yl]-amine

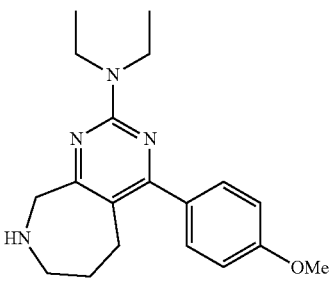 [SMILES: CCN(CC)c1nc2c(c(-c3ccc(OC)cc3)n1)CCCNC2]

HPLC: R$_t$=9.5 min. MS (ESI): mass calcd. for C$_{19}$H$_{26}$N$_4$O, 326.4; m/z found, 327.4 [M+H]$^+$. $^1$H NMR (CDCl$_3$): 7.46 (d, J=8.7, 2H), 6.95 (d, J=8.7, 2H), 3.95 (s, 2H), 3.85 (s, 3H), 3.64 (q, J=7.0, 4H), 3.21-3.17 (m, 2H), 2.84-2.81 (m, 2H), 1.71-1.66 (m, 2H), 1.17 (t, J=7.0, 6H).

Example 4

4-(2-Diethylamino-6,7,8,9-tetrahydro-5H-pyrimido[4,5-c]azepin-4-yl)-benzonitrile

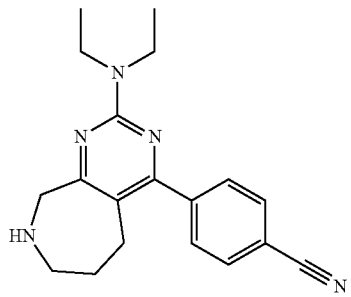 [SMILES: CCN(CC)c1nc2c(c(-c3ccc(C#N)cc3)n1)CCCNC2]

HPLC: R$_t$=9.7 min. MS (ESI): mass calcd. for C$_{19}$H$_{23}$N$_5$, 321.4; m/z found, 322.4 [M+H]$^+$. $^1$H NMR (CDCl$_3$): 7.74 (d, J=8.3, 2H), 7.59 (d, J=8.4, 2H), 3.99 (s, 2H), 3.64 (q, J=7.0, 4H), 3.23-3.20 (m, 2H), 2.74-2.72 (m, 2H), 1.74-1.68 (m, 2H), 1.18 (t, J=7.0, 6H).

Example 5

4-(4-Methoxy-phenyl)-2-(2-methyl-piperidin-1-yl)-6,7,8,9-tetrahydro-5H-pyrimido[4,5-c]azepine hydrochloride

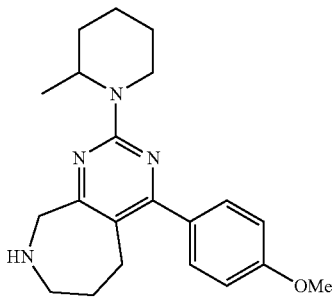 [SMILES: COc1ccc(-c2nc(N3CCCCC3C)nc3c2CCCNC3)cc1]

HPLC: R$_t$=10.1 min. MS (ESI): mass calcd. for O$_{21}$H$_{28}$N$_4$O, 352.5; m/z found, 353.4 [M+H]$^+$. $^1$H NMR (MeOH-d$_4$): 7.50 (d, J=8.7, 2H), 7.09 (d, J=8.7, 2H), 5.09 (s, 1H), 4.55 (d, J=11.7, 1H), 4.46 (s, 2H), 3.88 (s, 3H), 3.56-3.49 (m, 2H), 3.14 (t, J=13.1, 1H), 2.97-2.92 (m, 2H), 2.05-1.98 (m, 2H), 1.84-1.44 (m, 6H), 1.27 (d, J=6.9, 3H).

Example 6

4-(4-Fluoro-phenyl)-2-(2-methyl-piperidin-1-yl)-6,7,8,9-tetrahydro-5H-pyrimido[4,5-c]azepine

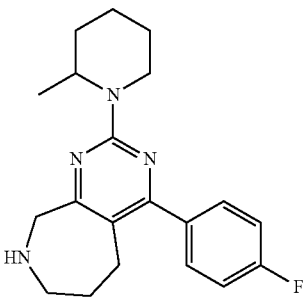 [SMILES: CC1CCCCN1c1nc2c(c(-c3ccc(F)cc3)n1)CCCNC2]

HPLC: R$_t$=10.4 min. MS (ESI): mass calcd. for C$_{20}$H$_{25}$FN$_4$, 340.5; m/z found, 341.4 [M+H]$^+$. $^1$H NMR (CDCl$_3$): 7.47 (dd, J=8.7, 5.5, 2H), 7.11 (t, J=8.7, 2H), 5.14-5.07 (m, 1H), 4.65 (d, J=13.4, 1H), 3.96 (s, 2H), 3.21-3.17 (m, 2H), 2.91 (ddd, J=13.3, 13.1, 2.8, 1H), 2.78 (dd, J=7.2, 2.3, 2H), 1.73-1.54 (m, 8H), 1.16 (d, J=6.9, 3H).

Example 7

4-[2-(2-Methyl-piperidin-1-yl)-6,7,8,9-tetrahydro-5H-pyrimido[4,5-c]azepin-4-yl]-benzonitrile

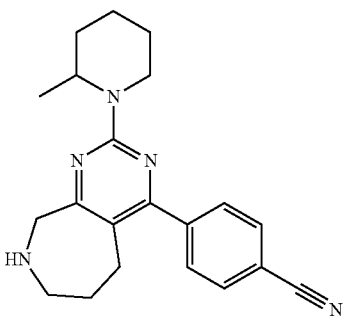 [SMILES: CC1CCCCN1c1nc2c(c(-c3ccc(C#N)cc3)n1)CCCNC2]

HPLC: R$_t$=10.2 min. MS (ESI): mass calcd. for O$_{21}$H$_{25}$N$_5$, 347.5; m/z found, 348.4 [M+H]$^+$. $^1$H NMR (CDCl$_3$): 7.72 (d, J=8.4, 2H), 7.58 (d, J=8.4, 2H), 5.11-5.05 (m, 1H), 4.64 (d, J=13.6, 1H), 3.96 (s, 2H), 3.21-3.17 (m, 2H), 2.91 (ddd, J=13.3, 13.1, 2.8, 1H), 2.73 (dd, J=7.7, 3.1, 2H), 1.74-1.62 (m, 8H), 1.16 (d, J=6.9, 3H).

Example 8

2-(2-Methyl-piperidin-1-yl)-4-p-tolyl-6,7,8,9-tetrahydro-5H-pyrimido[4,5-c]azepine

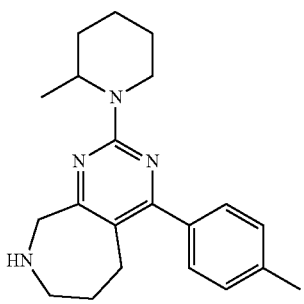 [SMILES: Cc1ccc(-c2nc(N3CCCCC3C)nc3c2CCCNC3)cc1]

HPLC: R$_t$=10.3 min. MS (ESI): mass calcd. for C$_{18}$H$_{28}$N$_4$, 336.5; m/z found, 337.4 [M+H]$^+$. $^1$H NMR (CDCl$_3$): 7.39 (d, J=8.1, 2H), 7.23 (d, J=7.8, 2H), 5.16-5.09 (m, 1H), 4.67 (d, J=13.3, 1H), 3.95 (s, 2H), 3.20-3.17 (m, 2H), 2.91 (ddd, J=13.2, 13.1, 2.7, 1H), 2.80 (dd, J=7.5, 2.6, 2H), 2.40 (s, 3H), 1.73-1.39 (m, 8H), 1.16 (d, J=6.9, 3H).

Example 9

Diethyl-[4-(4-fluoro-phenyl)-6,7,8,9-tetrahydro-5H-pyrimido[4,5-d]azepin-2-yl]-amine hydrochloride

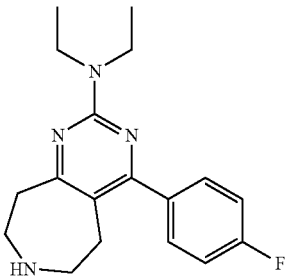 [SMILES: CCN(CC)c1nc2c(c(-c3ccc(F)cc3)n1)CCNCC2]

Step A: 5-oxo-azepane-1,4-dicarboxylic acid 1-tert-butyl ester 4-ethyl ester

The title compound was prepared from 4-oxo-piperidine-1-carboxylic acid tert-butyl ester using methods analogous to those described in Example 1, Step A.

Step B

The title compound was synthesized according to Example 1, Steps B-D. HPLC: R$_t$=8.9 min. MS (ESI): mass calcd. for C$_{18}$H$_{23}$FN$_4$, 314.4; m/z found, 315.3 [M+H]$^+$. $^1$H NMR (MeOH-d$_4$): 7.63 (s, 2H), 7.30 (t, J=8.3, 2H), 3.77 (q, J=6.4, 4H), 3.51 (d, J=14.1, 4H), 3.37 (s, 2H), 3.09 (s, 2H), 1.28 (t, J=6.8, 6H).

The compounds in Examples 10-14 were prepared using methods similar to those described in Example 9.

Example 10

Diethyl-(4-pyridin-4-yl-6,7,8,9-tetrahydro-5H-pyrimido[4,5-d]azepin-2-yl)-amine hydrochloride

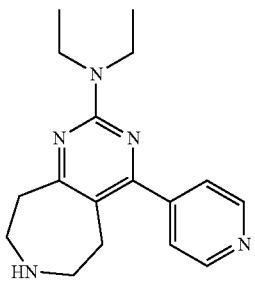 [SMILES: CCN(CC)c1nc2c(c(-c3ccncc3)n1)CCNCC2]

HPLC: R$_t$=7.1 min. MS (ESI): mass calcd. for C$_{17}$H$_{23}$N$_5$, 297.4; m/z found, 298.3 [M+H]$^+$. $^1$H NMR (MeOH-d$_4$): 8.62 (dd, J=4.5, 1.6, 2H), 7.49 (dd, J=4.5, 1.6, 2H), 3.65 (q, J=7.0, 4H), 3.04 (dd, J=6.7, 2.8, 2H), 3.00-2.96 (m, 2H), 2.87-2.84 (m, 2H), 2.76 (dd, J=6.4, 3.0, 2H), 1.17 (t, J=7.0, 6H).

Example 11

Diethyl-(4-p-tolyl-6,7,8,9-tetrahydro-5H-pyrimido[4,5-d]azepin-2-yl)-amine hydrochloride

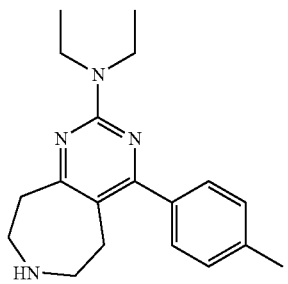 [SMILES: CCN(CC)c1nc2c(c(-c3ccc(C)cc3)n1)CCNCC2]

HPLC: $R_t$=8.8 min. MS (ESI): mass calcd. for $C_{19}H_{26}N_4$, 310.5; m/z found, 311.4 [M+H]$^+$. $^1$H NMR (MeOH-d$_4$): 7.37 (d, J=8.1, 2H), 7.31 (d, J=8.0, 2H), 3.69 (q, J=7.0, 4H), 3.46-3.41 (m, 2H), 3.34-3.27 (m, 4H), 3.09-3.04 (m, 2H), 2.41 (s, 3H), 1.20 (t, J=7.0, 6H).

Example 12

Diethyl-(4-thiophen-3-yl-6,7,8,9-tetrahydro-5H-pyrimido[4,5-d]azepin-2-yl)-amine hydrochloride

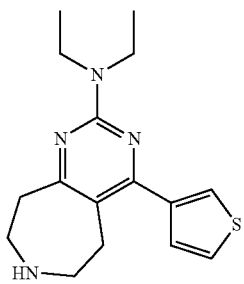 [SMILES: CCN(CC)c1nc2c(c(-c3ccsc3)n1)CCNCC2]

HPLC: $R_t$=8.3 min. MS (ESI): mass calcd. for $C_{16}H_{22}N_4S$, 302.4; m/z found, 303.3 [M+H]$^+$. $^1$H NMR (MeOH-d$_4$): 7.55 (dd, J=3.0, 1.2, 1H), 7.46 (dd, J=5.0, 3.0, 1H), 7.28 (dd, J=5.0, 1.3, 1H), 3.64 (q, J=7.0, 4H), 2.99 (dd, J=16.3, 7.6, 4H), 2.90 (dt, J=9.7, 3.6, 4H), 1.17 (t, J=7.0, 6H).

Example 13

Diethyl-[4-(4-methoxy-phenyl)-6,7,8,9-tetrahydro-5H-pyrimido[4,5-d]azepin-2-yl]-amine hydrochloride

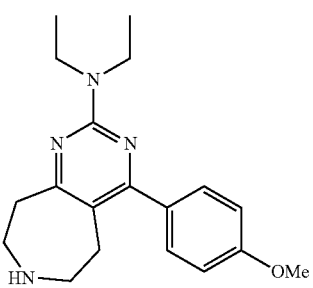 [SMILES: CCN(CC)c1nc2c(c(-c3ccc(OC)cc3)n1)CCNCC2]

HPLC: $R_t$=8.2 min. MS (ESI): mass calcd. for $C_{19}H_{26}N_4O$, 326.5; m/z found, 327.4 [M+H]$^+$. $^1$H NMR (MeOH-d$_4$): 7.53 (d, J=8.7, 2H), 7.11 (d, J=8.7, 2H), 3.89 (s, 3H), 3.77 (q, J=7.0, 4H), 3.51 (d, J=7.9, 2H), 3.47-3.43 (m, 2H), 3.40-3.33 (m, 2H), 3.13-3.10 (m, 2H), 1.28 (t, J=7.1, 6H).

Example 14

4-(2-Diethylamino-6,7,8,9-tetrahydro-5H-pyrimido[4,5-d]azepin-4-yl)-benzonitrile hydrochloride

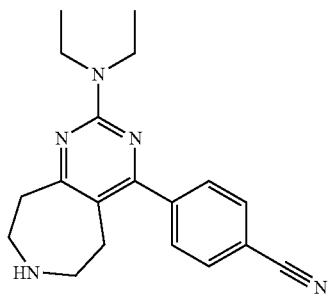 [SMILES: CCN(CC)c1nc2c(c(-c3ccc(C#N)cc3)n1)CCNCC2]

HPLC: $R_t$=9.3 min. MS (ESI): mass calcd. for $C_{19}H_{23}N_5$, 321.4; m/z found, 322.4 [M+H]$^+$. $^1$H NMR (MeOH-d$_4$): 7.83 (d, J=8.2, 2H), 7.63 (d, J=8.2, 2H), 3.65 (q, J=7.0, 4H), 3.24 (d, J=6.9, 2H), 3.19-3.15 (m, 2H), 3.12-3.08 (m, 2H), 2.89 (dd, J=6.2, 3.7, 2H), 1.16 (t, J=7.0, 6H).

Example 15

Diethyl-[4-(4-fluoro-phenyl)-6,7,8,9-tetrahydro-5H-1,3,6-triaza-benzocyclohepten-2-yl]-amine

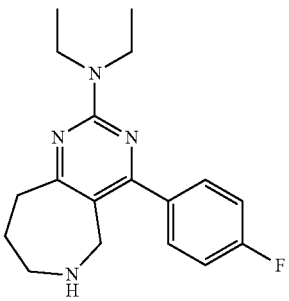 [SMILES: CCN(CC)c1nc2c(c(-c3ccc(F)cc3)n1)CNCCC2]

The title compound was prepared from 4-oxo-azepane-1,3-dicarboxylic acid 1-tert-butyl ester 3-ethyl ester using methods analogous to those described in Example 1, Steps A-D. HPLC: $R_t$=9.4 min. MS (ESI): mass calcd. for $C_{18}H_{23}FN_4$, 314.4; m/z found, 315.4 [M+H]$^+$. $^1$H NMR (CDCl$_3$): 7.51 (dd, J=8.7, 5.5, 2H), 7.09 (t, J=8.7, 2H), 3.85 (s, 2H), 3.65 (q, J=7.0, 4H), 3.21-3.17 (m, 2H), 3.00 (d, J=11.5, 2H), 1.86-1.80 (m, 2H), 1.18 (t, J=7.0, 6H).

The compounds in Examples 16-22 were prepared using methods similar to those described in Example 15. Hydrochloride salts were prepared as described in Example 1, Step E.

Example 16

Diethyl-(4-p-tolyl-6,7,8,9-tetrahydro-5H-1,3,6-triaza-benzocyclohepten-2-yl)-amine

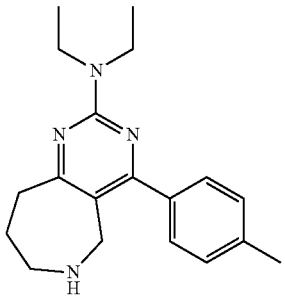 [SMILES: CCN(CC)c1nc2c(c(-c3ccc(C)cc3)n1)CNCCC2]

HPLC: $R_t$=9.3 min. MS (ESI): mass calcd. for $C_{19}H_{26}N_4$, 310.5; m/z found, 311.4 [M+H]$^+$. $^1$H NMR (CDCl$_3$): 7.42 (d, J=8.1, 2H), 7.22 (d, J=7.8, 2H), 3.86 (s, 2H), 3.66 (q, J=7.0, 4H), 3.20-3.16 (m, 2H), 2.99 (d, J=11.4, 2H), 2.39 (s, 3H), 1.84-1.77 (m, 2H), 1.17 (t, J=7.0, 6H).

Example 17

Diethyl-[4-(4-methoxy-phenyl)-6,7,8,9-tetrahydro-5H-1,3,6-triaza-benzocyclohepten-2-yl]-amine

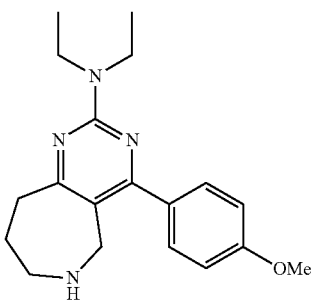 [SMILES: CCN(CC)c1nc2c(c(-c3ccc(OC)cc3)n1)CNCCC2]

HPLC: $R_t$=8.9 min. MS (ESI): mass calcd. for $C_{19}H_{26}N_4O$, 326.5; m/z found, 327.4 [M+H]$^+$. $^1$H NMR (CDCl$_3$): 7.49 (d, J=8.7, 2H), 6.94 (d, J=8.7, 2H), 3.88 (s, 2H), 3.84 (s, 3H), 3.66 (q, J=7.0, 4H), 3.20-3.16 (m, 2H), 2.99 (d, J=11.4, 2H), 1.83-1.77 (m, 2H), 1.18 (t, J=7.0, 6H).

Example 18

4-(2-Diethylamino-6,7,8,9-tetrahydro-5H-1,3,6-triaza-benzocyclohepten-4-yl)-benzonitrile

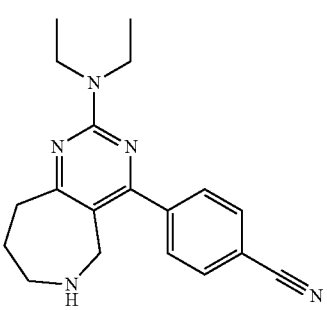 [SMILES: CCN(CC)c1nc2c(c(-c3ccc(C#N)cc3)n1)CNCCC2]

HPLC: $R_t$=9.5 min. MS (ESI): mass calcd. for $C_{19}H_{23}N_5$, 321.4; m/z found, 322.4 [M+H]$^+$. $^1$H NMR (CDCl$_3$): 7.71 (d, J=8.5, 2H), 7.63 (d, J=8.5, 2H), 3.78 (s, 2H), 3.64 (q, J=7.0, 4H), 3.21-3.17 (m, 2H), 3.03-2.99 (m, 2H), 1.86-1.78 (m, 2H), 1.17 (t, J=7.0, 6H).

Example 19

2-Piperidin-1-yl-4-p-tolyl-6,7,8,9-tetrahydro-5H-1,3,6-triaza-benzocycloheptene

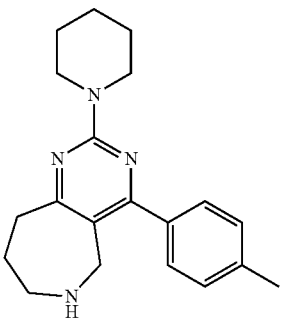 [SMILES: Cc1ccc(-c2nc(N3CCCCC3)nc3c2CNCCC3)cc1]

HPLC: $R_t$=9.5 min. MS (ESI): mass calcd. for $C_{20}H_{26}N_4$, 322.5; m/z found, 323.4 [M+H]$^+$. $^1$H NMR (CDCl$_3$): 7.42 (d, J=8.0, 2H), 7.22 (d, J=7.9, 2H), 3.87 (s, 2H), 3.82-3.79 (m, 4H), 3.20-3.17 (m, 2H), 3.00 (d, J=11.4, 2H), 2.39 (s, 3H), 1.85-1.79 (m, 2H), 1.67-1.62 (m, 2H), 1.61-1.56 (m, 4H).

Example 20

4-(4-Fluoro-phenyl)-2-piperidin-1-yl-6,7,8,9-tetrahydro-5H-1,3,6-triaza-benzocycloheptene hydrochloride

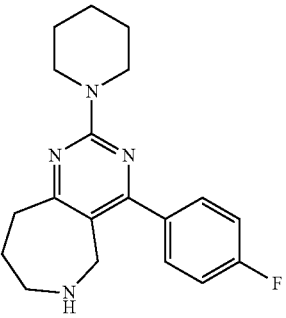 [SMILES: Fc1ccc(-c2nc(N3CCCCC3)nc3c2CNCCC3)cc1]

HPLC: $R_t$=9.5 min. MS (ESI): mass calcd. for $C_{19}H_{23}FN_4$, 326.4; m/z found, 327.4 [M+H]$^+$. $^1$H NMR (MeOH-d$_4$): 7.66 (dd, J=8.5, 5.3, 2H), 7.33 (t, J=8.7, 2H), 4.30 (s, 2H), 3.91 (s, 4H), 3.55-3.51 (m, 2H), 3.29-3.24 (m, 2H), 2.19-2.13 (m, 2H), 1.81-1.73 (m, 2H), 1.73-1.65 (m, 4H).

Example 21

4-(4-Methoxy-phenyl)-2-piperidin-1-yl-6,7,8,9-tetrahydro-5H-1,3,6-triaza-benzocycloheptene hydrochloride

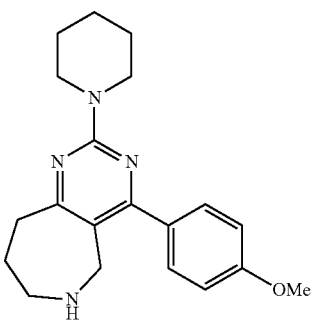 [SMILES: COc1ccc(-c2nc(N3CCCCC3)nc3c2CNCCC3)cc1]

HPLC: R$_f$=9.1 min. MS (ESI): mass calcd. for C$_{20}$H$_{26}$N$_4$O, 338.5; m/z found, 339.4 [M+H]$^+$. $^1$H NMR (MeOH-d$_4$): 7.57 (d, J=7.9, 2H), 7.13 (d, J=8.6, 2H), 4.35 (s, 2H), 3.94-3.90 (m, 4H), 3.89 (s, 3H), 3.55-3.51 (m, 2H), 3.29-3.24 (m, 2H), 2.16 (s, 2H), 1.83-1.65 (m, 6H)

Example 22

4-(2-Piperidin-1-yl-6,7,8,9-tetrahydro-5H-1,3,6-triaza-benzocyclohepten-4-yl)-benzonitrile hydrochloride

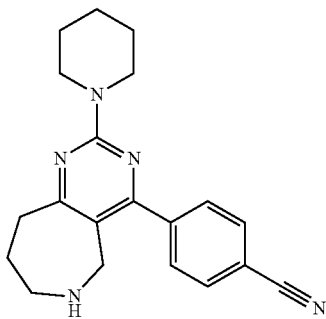 [SMILES: N#Cc1ccc(-c2nc(N3CCCCC3)nc3c2CNCCC3)cc1]

HPLC: R$_f$=9.5 min. MS (ESI): mass calcd. for C$_{20}$H$_{23}$N$_5$, 333.4; m/z found, 334.3 [M+H]$^+$. $^1$H NMR (MeOH-d$_4$): 7.93 (d, J=8.0, 2H), 7.75 (d, J=8.2, 2H), 4.25 (s, 2H), 3.92-3.88 (m, 4H), 3.53-3.50 (m, 2H), 3.35 (s, 1H), 3.27-3.23 (m, 2H), 2.17-2.10 (m, 2H), 1.78-1.72 (m, 2H), 1.69-1.63 (m, 4H).

Example 23

[7-Benzyl-4-(4-fluoro-phenyl)-5,6,7,8-tetrahydro-pyrido[3,4-d]pyrimidin-2-yl]-diethyl-amine

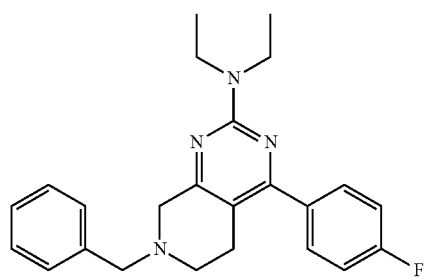 [SMILES: CCN(CC)c1nc2c(c(-c3ccc(F)cc3)n1)CCN(Cc1ccccc1)C2]

Step A: 7-Benzyl-2-diethylamino-5,6,7,8-tetrahydro-pyrido[3,4-d]pyrimidin-4-ol

To a solution of 1-benzyl-3-oxo-piperidine-4-carboxylic acid ethyl ester hydrochloride (2.11 g, 7.1 mmol) in EtOH (35 mL) was added diethyl guanidinium trifluoroacetate (1.5 g, 7.1 mmol) and sodium ethoxide (21 wt % in EtOH, 6.7 mL). The reaction was heated at reflux for 16 h then cooled to room temperature (rt). The reaction mixture was diluted with H$_2$O and extracted with CH$_2$Cl$_2$ (2×). The combined organic extracts were dried and concentrated. The resulting material was triturated with Et$_2$O to give the title compound (1.54 g, 70%) as a light brown solid. MS (ESI): mass calcd. for C$_{18}$H$_{24}$N$_4$O, 312.4; m/z found, 313.3 [M+H]$^+$.

Step B: Trifluoro-methanesulfonic acid 7-benzyl-2-diethylamino-5,6,7,8-tetrahydro-pyrido[3,4-d]pyrimidin-4-yl ester To a solution of 7-benzyl-2-diethylamino-5,6,7,8-tetrahydro-pyrido[3,4-d]pyrimidin-4-ol (0.60 g, 1.9 mmol) in CH$_2$Cl$_2$ (20 mL) at 0° C. was added Et$_3$N (0.21 g, 0.30 mL, 2.1 mmol) followed by triflic anhydride (0.60 g, 0.36 mL, 2.1 mmol). After 1 h, the mixture was diluted with H$_2$O and extracted with CH$_2$Cl$_2$ (2×). The combined organic layers were dried and concentrated. Purification by FCC provided the title compound (0.66 g, 78%) as a clear oil. MS (ESI): mass calcd. for C$_{19}$H$_{23}$F$_3$N$_4$O$_3$S, 444.5; m/z found, 445.2 [M+H]$^+$.

Step C: [7-Benzyl-4-(4-fluoro-phenyl)-5,6,7,8-tetrahydro-pyrido[3,4-d]pyrimidin-2-yl]-diethyl-amine To trifluoro-methanesulfonic acid 7-benzyl-2-diethylamino-5,6,7,8-tetrahydro-pyrido[3,4-d]pyrimidin-4-yl ester (0.14 g, 0.31 mmol) was added 4-fluoroboronic acid (0.066 g, 0.47 mmol), K$_3$PO$_4$ (0.099 g, 0.47 mmol), Pd(dppf)Cl$_2$ (0.013 g, 0.016 mmol), and dppf (0.009 g, 0.016 mmol). The flask was fitted with a reflux condenser, evacuated under vacuum and refilled with N$_2$. Dioxane (4 mL) was added and the mixture was heated at 100° C. for 3 h, then cooled to rt and diluted with Et$_2$O. The mixture was filtered through a small pad of SiO$_2$. The filtrate was concentrated and purified by FCC to provide the title compound (0.101 g, 82%) as a light yellow clear oil. HPLC: R$_f$=11.2 min. MS (ESI): mass calcd. for C$_{24}$H$_{27}$FN$_4$, 390.5; m/z found, 391.4 [M+H]$^+$. $^1$H NMR (CDCl$_3$): 7.62 (dd, J=8.8, 5.5, 2H), 7.40 (d, J=7.1, 2H), 7.35 (t, J=7.4, 2H), 7.29 (d, J=7.2, 1H), 7.10 (t, J=8.7, 2H), 3.69 (s, 2H), 3.62 (q, J=7.0, 4H), 3.58 (s, 2H), 2.73 (t, J=5.6, 2H), 2.64 (t, J=5.6, 2H), 1.17 (t, J=7.0, 6H).

Example 24

Diethyl-[4-(4-fluoro-phenyl)-5,6,7,8-tetrahydro-pyrido[3,4-d]pyrimidin-2-yl]-amine

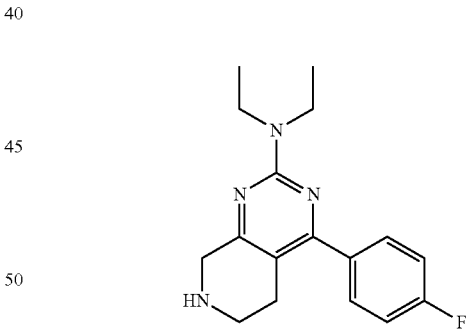

To a solution of [7-benzyl-4-(4-fluoro-phenyl)-5,6,7,8-tetrahydro-pyrido[3,4-d]pyrimidin-2-yl]-diethyl-amine (0.052 g, 0.13 mmol) in EtOH (1.5 mL) was added 10 wt % Pd/C and 1,4-cyclohexadiene (0.062 mL, 0.66 mmol). The mixture was heated at 85° C. for 2 h and cooled to rt. The mixture was concentrated and the residue was purified by FCC (2 M NH$_3$/MeOH in CH$_2$Cl$_2$) to afford the title compound. HPLC: R$_f$=9.7 min. MS (ESI): mass calcd. for C$_{17}$H$_{21}$FN$_4$, 300.4; m/z found, 301.4 [M+H]$^+$. $^1$H NMR (CDCl$_3$): 7.60 (dd, J=8.8, 5.5, 2H), 7.11 (t, J=8.8, 2H), 3.93 (s, 2H), 3.63 (q, J=7.0, 4H), 3.02 (t, J=5.7, 2H), 2.64 (t, J=5.7, 2H), 1.18 (t, J=7.0, 6H).

The compounds in Examples 25-38 were prepared using methods similar to those described in Examples 23-24.

Example 25

(7-Benzyl-4-p-tolyl-5,6,7,8-tetrahydro-pyrido[3,4-d]pyrimidin-2-yl)-diethyl-amine

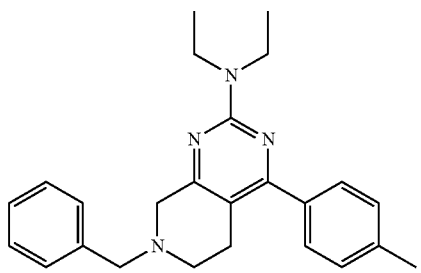 [SMILES: CCN(CC)c1nc2c(c(-c3ccc(C)cc3)n1)CCN(Cc1ccccc1)C2]

HPLC: $R_t$=11.5 min. MS (ESI): mass calcd. for $C_{25}H_{30}N_4$, 386.5; m/z found, 387.4 [M+H]$^+$. $^1$H NMR (CDCl$_3$): 7.53 (d, J=8.1, 2H), 7.40 (d, J=7.0, 2H), 7.34 (t, J=7.4, 2H), 7.28 (d, J=7.3, 1H), 7.23 (d, J=7.9, 2H), 3.68 (s, 2H), 3.62 (q, J=7.0, 4H), 3.58 (s, 2H), 2.75 (t, J=5.6, 2H), 2.63 (t, J=5.7, 2H), 2.39 (s, 3H), 1.16 (t, J=7.0, 6H).

Example 26

Diethyl-(4-p-tolyl-5,6,7,8-tetrahydro-pyrido[3,4-d]pyrimidin-2-yl)-amine

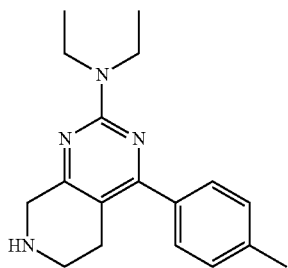 [SMILES: CCN(CC)c1nc2c(c(-c3ccc(C)cc3)n1)CCNC2]

HPLC: $R_t$=9.8 min. MS (ESI): mass calcd. for $C_{18}H_{24}N_4$, 296.4; m/z found, 297.4 [M+H]$^+$. $^1$H NMR (CDCl$_3$): 7.51 (d, J=8.1, 2H), 7.24 (d, J=7.9, 2H), 3.92 (s, 2H), 3.64 (q, J=7.0, 4H), 3.00 (t, J=5.7, 2H), 2.66 (t, J=5.7, 2H), 2.40 (s, 3H), 1.17 (t, J=7.0, 6H).

Example 27

[7-Benzyl-4-(4-methoxy-phenyl)-5,6,7,8-tetrahydro-pyrido[3,4-d]pyrimidin-2-yl]-diethyl-amine

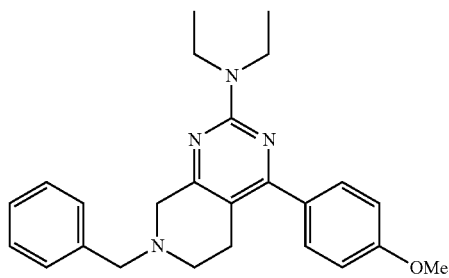 [SMILES: CCN(CC)c1nc2c(c(-c3ccc(OC)cc3)n1)CCN(Cc1ccccc1)C2]

HPLC: $R_t$=11.1 min. MS (ESI): mass calcd. for $C_{25}H_{30}N_4O$, 402.5; m/z found, 403.4 [M+H]$^+$. $^1$H NMR (CDCl$_3$): 7.65 (d, J=8.8, 2H), 7.44 (d, J=7.2, 2H), 7.38 (t, J=7.5, 2H), 7.32 (d, J=7.4, 1H), 6.98 (d, J=8.8, 2H), 3.88 (s, 3H), 3.72 (s, 2H), 3.66 (q, J=7.0, 4H), 3.61 (s, 2H), 2.81 (t, J=5.6, 2H), 2.67 (t, J=5.6, 2H), 1.20 (t, J=7.0, 6H).

Example 28

Diethyl-[4-(4-methoxy-phenyl)-5,6,7,8-tetrahydro-pyrido[3,4-d]pyrimidin-2-yl]-amine

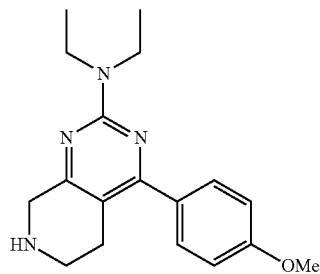 [SMILES: CCN(CC)c1nc2c(c(-c3ccc(OC)cc3)n1)CCNC2]

HPLC: $R_t$=9.0 min. MS (ESI): mass calcd. for $C_{18}H_{24}N_4O$, 312.4; m/z found, 313.4 [M+H]$^+$. $^1$H NMR (CDCl$_3$): 7.60 (d, J=8.9, 2H), 6.95 (d, J=8.8, 2H), 3.92 (s, 2H), 3.85 (s, 3H), 3.64 (q, J=7.0, 4H), 3.01 (t, J=5.7, 2H), 2.68 (t, J=5.7, 2H), 1.18 (t, J=7.0, 6H).

Example 29

4-(7-Benzyl-2-diethylamino-5,6,7,8-tetrahydro-pyrido[3,4-d]pyrimidin-4-yl)-benzonitrile

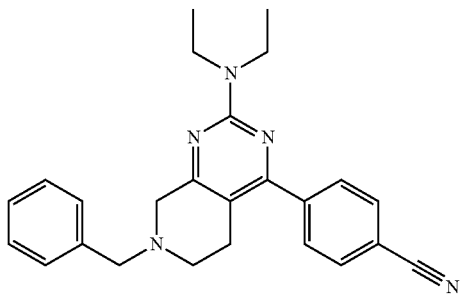 [SMILES: CCN(CC)c1nc2c(c(-c3ccc(C#N)cc3)n1)CCN(Cc1ccccc1)C2]

HPLC: $R_t$=11.0 min. MS (ESI): mass calcd. for $C_{25}H_{27}N_5$, 397.5; m/z found, 398.4 [M+H]$^+$. $^1$H NMR (CDCl$_3$): 7.71 (s, 4H), 7.39 (d, J=7.02, 2H), 7.34 (t, J=7.4, 2H), 7.29 (d, J=7.2, 1H), 3.69 (s, 2H), 3.61 (dd, J=14.0, 7.0, 4H), 3.58 (s, 2H), 2.69 (t, J=5.3, 2H), 2.64 (t, J=5.3, 2H), 1.16 (t, J=7.0, 6H).

Example 30

4-(2-Diethylamino-5,6,7,8-tetrahydro-pyrido[3,4-d]pyrimidin-4-yl)-benzonitrile

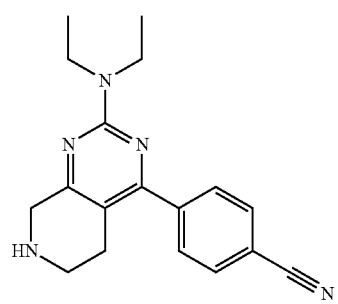 [SMILES: CCN(CC)c1nc2c(c(-c3ccc(C#N)cc3)n1)CCNC2]

HPLC: $R_t$=9.6 min. MS (ESI): mass calcd. for $C_{18}H_{21}N_5$, 307.4; m/z found, 308.3 [M+H]$^+$. $^1$H NMR (CDCl$_3$): 7.72 (d, J=8.4, 2H), 7.69 (d, J=8.4, 2H), 3.93 (s, 2H), 3.62 (q, J=7.0, 4H), 3.02 (t, J=5.7, 2H), 2.60 (t, J=5.7, 2H), 1.17 (t, J=7.0, 6H).

Example 31

2-Azepan-1-yl-7-benzyl-4-(4-fluoro-phenyl)-5,6,7,8-tetrahydro-pyrido[3,4-d]pyrimidine

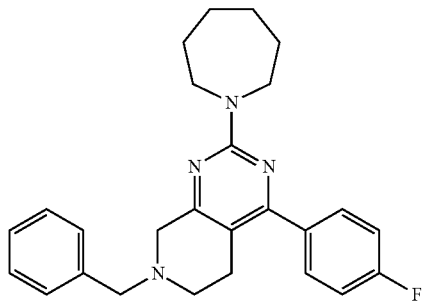 [SMILES: Fc1ccc(-c2nc(N3CCCCCC3)nc3c2CCN(Cc2ccccc2)C3)cc1]

HPLC: $R_t$=11.9 min. MS (ESI): mass calcd. for $C_{26}H_{29}FN_4$, 416.6; m/z found, 417.4 [M+H]$^+$. $^1$H NMR (CDCl$_3$): 7.62 (dd, J=8.8, 5.5, 2H), 7.40 (d, J=7.0, 2H), 7.35 (t, J=7.4, 2H), 7.29 (d, J=7.3, 1H), 7.10 (t, J=8.8, 2H), 3.76-3.73 (m, 4H), 3.69 (s, 2H), 3.58 (s, 2H), 2.73 (t, J=5.6, 2H), 2.64 (t, J=5.6, 2H), 1.78-1.73 (m, 4H), 1.55-1.52 (m, 4H).

Example 32

2-Azepan-1-yl-4-(4-fluoro-phenyl)-5,6,7,8-tetrahydro-pyrido[3,4-d]pyrimidine

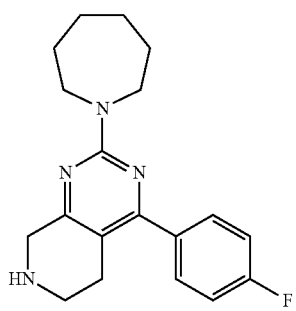 [SMILES: Fc1ccc(-c2nc(N3CCCCCC3)nc3c2CCNC3)cc1]

HPLC: $R_t$=10.1 min. MS (ESI): mass calcd. for $C_{26}H_{23}FN_4$, 326.4; m/z found, 327.4 [M+H]$^+$. $^1$H NMR (CDCl$_3$): 7.60 (dd, J=8.8, 5.5, 2H), 7.11 (t, J=8.7, 2H), 3.93 (s, 2H), 3.77-3.74 (m, 4H), 3.02 (t, J=5.7, 2H), 2.64 (t, J=5.7, 2H), 1.80-1.74 (m, 4H), 1.56-1.53 (m, 4H).

Example 33

2-Azepan-1-yl-7-benzyl-4-p-tolyl-5,6,7,8-tetrahydro-pyrido[3,4-d]pyrimidine

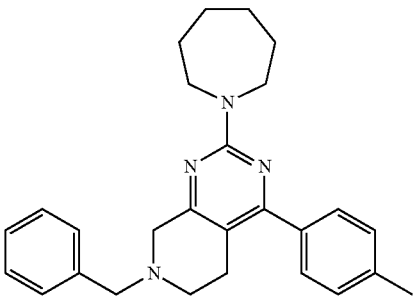 [SMILES: Cc1ccc(-c2nc(N3CCCCCC3)nc3c2CCN(Cc2ccccc2)C3)cc1]

HPLC: $R_t$=12.0 min. MS (ESI): mass calcd. for $C_{27}H_{32}N_4$, 412.6; m/z found, 413.4 [M+H]$^+$. $^1$H NMR (CDCl$_3$): 7.53 (d, J=8.1, 2H), 7.40 (d, J=7.3, 2H), 7.34 (t, J=7.5, 2H), 7.28 (d, J=7.3, 1H), 7.23 (d, J=7.9, 2H), 3.76-3.73 (m, 4H), 3.69 (s, 2H), 3.58 (s, 2H), 2.76 (t, J=5.6, 2H), 2.64 (t, J=5.6, 2H), 2.39 (s, 3H), 1.79-1.72 (m, 4H), 1.55-1.52 (m, 4H).

Example 34

2-Azepan-1-yl-4-p-tolyl-5,6,7,8-tetrahydro-pyrido[3,4-d]pyrimidine

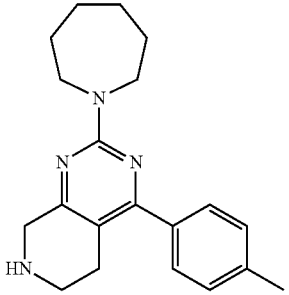 [SMILES: Cc1ccc(-c2nc(N3CCCCCC3)nc3c2CCNC3)cc1]

HPLC: $R_t$=10.2 min. MS (ESI): mass calcd. for $C_{20}H_{26}N_4$, 322.5; m/z found, 323.4 [M+H]$^+$. $^1$H NMR (CDCl$_3$): 7.51 (d, J=8.1, 2H), 7.24 (d, J=7.8, 2H), 3.92 (s, 2H), 3.78-3.74 (m, 4H), 3.01 (t, J=5.7, 2H), 2.66 (t, J=5.7, 2H), 2.40 (s, 3H), 1.79-1.73 (m, 4H), 1.56-1.53 (m, 4H).

Example 35

2-Azepan-1-yl-7-benzyl-4-(4-methoxy-phenyl)-5,6,7,8-tetrahydro-pyrido[3,4-d]pyrimidine

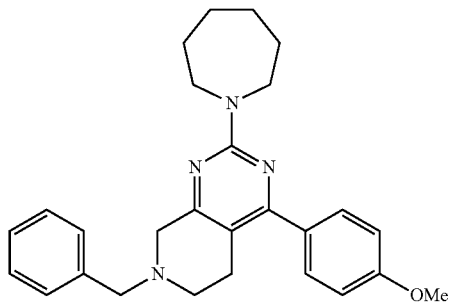 [SMILES: COc1ccc(-c2nc(N3CCCCCC3)nc3c2CCN(Cc2ccccc2)C3)cc1]

HPLC: $R_t$=11.6 min. MS (ESI): mass calcd. for $C_{27}H_{32}N_4O$, 428.6; m/z found, 429.4 [M+H]$^+$. $^1$H NMR (CDCl$_3$): 7.62 (d, J=8.8, 2H), 7.40 (d, J=7.0, 2H), 7.34 (t, J=7.3, 2H), 7.28 (d, J=7.2, 1H), 6.94 (d, J=8.8, 2H), 3.85 (s, 3H), 3.77-3.73 (m, 4H), 3.68 (s, 2H), 3.58 (s, 2H), 2.78 (t, J=5.6, 2H), 2.64 (t, J=5.6, 2H), 1.79-1.73 (m, 4H), 1.56-1.51 (m, 4H).

Example 36

2-Azepan-1-yl-4-(4-methoxy-phenyl)-5,6,7,8-tetrahydro-pyrido[3,4-d]pyrimidine

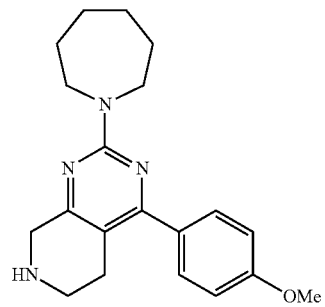 [SMILES: COc1ccc(-c2nc(N3CCCCCC3)nc3c2CCNC3)cc1]

HPLC: $R_t$=9.3 min. MS (ESI): mass calcd. for $C_{20}H_{26}N_4O$, 338.5; m/z found, 339.4 [M+H]$^+$. $^1$H NMR (CDCl$_3$): 7.60 (d, J=8.9, 2H), 6.95 (d, J=8.8, 2H), 3.92 (s, 2H), 3.85 (s, 3H), 3.78-3.75 (m, 4H), 3.02 (t, J=5.7, 2H), 2.69 (t, J=5.7, 2H), 1.80-1.75 (m, 4H), 1.56-1.53 (m, 4H).

Example 37

4-(2-Azepan-1-yl-7-benzyl-5,6,7,8-tetrahydro-pyrido[3,4-d]pyrimidin-4-yl)-benzonitrile

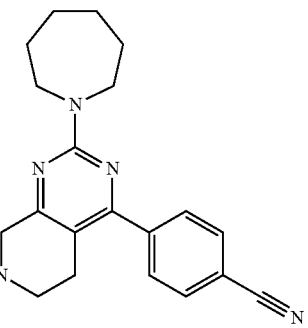

HPLC: $R_t$=11.5 min. MS (ESI): mass calcd. for $C_{27}H_{29}N_5$, 423.6; m/z found, 424.4 [M+H]$^+$. $^1$H NMR (CDCl$_3$): 7.71 (s, 4H), 7.38 (d, J=6.9, 2H), 7.34 (t, J=7.4, 2H), 6.84 (d, J=8.7, 1H), 3.74-3.71 (m, 4H), 3.69 (s, 2H), 3.59 (s, 2H), 2.68 (dd, J=13.6, 4.8, 4H), 1.78-1.72 (m, 4H), 1.55-1.52 (m, 4H).

Example 38

4-(4-Fluoro-phenyl)-2-(2-methyl-pyrrolidin-1-yl)-5,6,7,8-tetrahydro-pyrido[4,3-d]pyrimidine hydrochloride

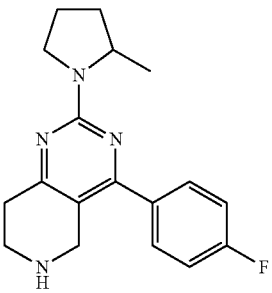 [SMILES: CC1CCCN1c1nc2c(c(-c3ccc(F)cc3)n1)CNCC2]

Step A: 4-(4-Fluoro-phenyl)-2-(2-methyl-pyrrolidin-1-yl)-7,8-dihydro-5H-pyrido[4,3-d]pyrimidine-6-carboxylic acid tert-butyl ester To a mixture of 3-(4-fluoro-benzoyl)-4-oxo-piperidine-1-carboxylic acid tert-butyl ester (0.20 g, 0.62 mmol) and 2-methyl-pyrrolidine-1-carboxamidine trifluoroacetate (0.14 g, 0.58 mmol) in MeCN (3 mL) was added K$_2$CO$_3$ (0.190 g, 1.4 mmol). The mixture was heated at reflux for 15 h, then cooled to rt, diluted with H$_2$O and extracted with CH$_2$Cl$_2$ (2×). The combined organic extracts were dried and concentrated. The residue was purified by FCC to give the title compound (0.193 g, 81%) as a clear oil. MS (ESI): mass calcd. for $C_{23}H_{29}FN_4O_2$, 412.5; m/z found, 413.4 [M+H]$^+$.

Step B: 4-(4-Fluoro-phenyl)-2-(2-methyl-pyrrolidin-1-yl)-5,6,7,8-tetrahydro-pyrido[4,3-d]pyrimidine hydrochloride To a solution of 4-(4-fluoro-phenyl)-2-(2-methyl-pyrrolidin-1-yl)-7,8-dihydro-5H-pyrido[4,3-d]pyrimidine-6-carboxylic acid tert-butyl ester (0.193 g, 0.47 mmol) in Et$_2$O (2 mL) was added 4 M HCl in dioxane (2.5 mL). After 16 h, the mixture was concentrated and the residue was triturated with Et$_2$O to give the title compound (0.124 g, 76%) as a white solid. MS (ESI): mass calcd. for $C_{18}H_{21}FN_4$, 312.4; m/z found, 313.4 [M+H]$^+$. $^1$H NMR (DMSO-d$_6$): 9.54 (m, 2H), 7.64 (dd, J=8.5, 5.5, 2H), 7.37 (t, J=8.8, 2H), 4.23-4.04 (m, 3H), 3.58-3.36 (m, 4H), 3.03-2.95 (m, 2H), 2.08-1.96 (m, 2H), 1.93-1.85 (m, 1H), 1.71-1.64 (m, 1H), 1.21 (d, J=6.3, 3H).

The compounds in Example 39-51 were prepared using methods analogous to those described in Example 38, Step A. Hydrochloride salts were prepared as in Example 38, Step B.

Example 39

[4-(4-Fluoro-phenyl)-5,6,7,8-tetrahydro-pyrido[4,3-d]pyrimidin-2-yl]-dimethyl-amine hydrochloride

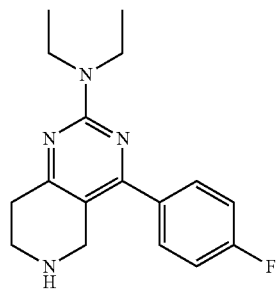 [SMILES: CCN(CC)c1nc2c(c(-c3ccc(F)cc3)n1)CNCC2]

HPLC: R$_f$=9.7 min. MS (ESI): mass calcd. for C$_{17}$H$_{21}$FN$_4$, 300.4; m/z found, 301.4 [M+H]$^+$. $^1$H NMR (DMSO-d$_6$): 9.66 (m, 2H), 7.65-7.62 (m, 2H), 7.40-7.35 (m, 2H), 4.09-4.07 (m, 2H), 3.60 (q, J=7.0, 4H), 3.44-3.37 (m, 2H), 2.98 (t, J=6.4, 2H), 1.13 (t, J=7.0, 6H).

Example 40

Diethyl-[4-(4-fluoro-phenyl)-5,6,7,8-tetrahydro-pyrido[4,3-d]pyrimidin-2-yl]-amine hydrochloride

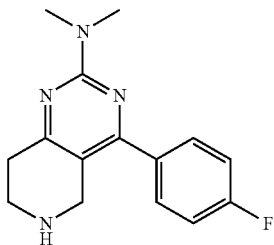 [SMILES: CN(C)c1nc2c(c(-c3ccc(F)cc3)n1)CNCC2]

HPLC: R$_f$=7.0 min. MS (ESI): mass calcd. for C$_{15}$H$_{17}$FN$_4$, 272.3; m/z found, 273.4 [M+H]$^+$. $^1$H NMR (DMSO-d$_6$): 9.63 (s, 2H), 7.64 (dd, J=8.8, 5.5, 2H), 7.37 (dd, J=8.9, 2H), 4.11-4.09 (m, 2H), 3.44-3.36 (m, 2H), 3.14 (s, 6H), 2.99 (dd, J=6.4, 2H).

Example 41

4-(4-Fluoro-phenyl)-2-pyrrolidin-1-yl-5,6,7,8-tetrahydro-pyrido[4,3-d]pyrimidine hydrochloride

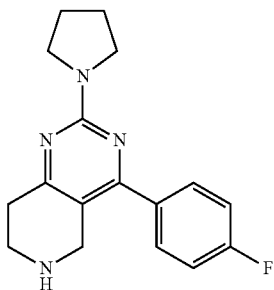 [SMILES: Fc1ccc(-c2nc(N3CCCC3)nc3c2CNCC3)cc1]

HPLC: R$_f$=7.9 min. MS (ESI): mass calcd. for C$_{17}$H$_{19}$FN$_4$, 298.2; m/z found, 299.4 [M+H]$^+$. $^1$H NMR (DMSO-d$_6$): 9.56 (s, 2H), 7.64 (dd, J=8.8, 5.5, 2H), 7.38 (t, J=8.9, 2H), 4.13-4.07 (m, 2H), 3.52-3.49 (m, 4H), 3.44-3.35 (m, 2H), 1.94-1.91 (m, 4H).

Example 42

4-(4-Fluoro-phenyl)-2-morpholin-4-yl-5,6,7,8-tetrahydro-pyrido[4,3-d]pyrimidine

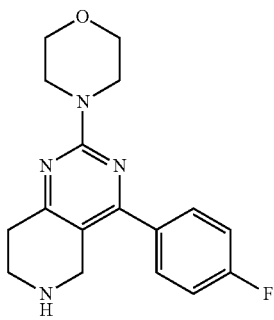 [SMILES: Fc1ccc(-c2nc(N3CCOCC3)nc3c2CNCC3)cc1]

HPLC: R$_f$=8.0 min. MS (ESI): mass calcd. for C$_{17}$H$_{19}$FN$_4$O, 314.4; m/z found, 315.4 [M+H]$^+$. $^1$H NMR (CDCl$_3$): 7.53 (dd, J=8.6, 5.5, 2H), 7.12 (t, J=8.6, 2H), 3.88 (s, 2H), 3.82-3.80 (m, 4H), 3.77-3.75 (m, 4H), 3.2 (t, J=6.0, 2H), 2.81 (t, J=6.0, 2H).

Example 43

[4-(4-Fluoro-phenyl)-5,6,7,8-tetrahydro-pyrido[4,3-d]pyrimidin-2-yl]-diisopropyl-amine hydrochloride

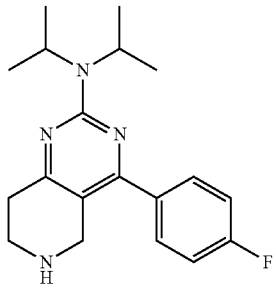 [SMILES: CC(C)N(c1nc2c(c(-c3ccc(F)cc3)n1)CNCC2)C(C)C]

MS (ESI): mass calcd. for C$_{19}$H$_{25}$FN$_4$, 328.2; m/z found, 329.4 [M+H]$^+$. $^1$H NMR (DMSO-d$_6$): 9.57 (s, 2H), 7.64 (dd, J=8.8, 5.3, 2H), 7.27 (t, J=8.7, 2H), 4.44 (br s, 2H), 4.08 (s, 2H), 3.44-3.36 (m, 2H), 2.96 (t, J=6.4, 2H), 1.29 (d, J=6.7, 12H).

Example 44

Ethyl-[4-(4-fluoro-phenyl)-5,6,7,8-tetrahydro-pyrido[4,3-d]pyrimidin-2-yl]-methyl-amine hydrochloride

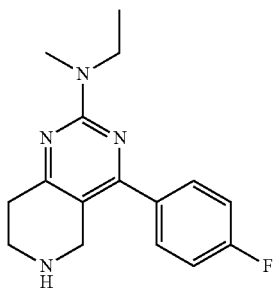 [SMILES: CCN(C)c1nc2c(c(-c3ccc(F)cc3)n1)CNCC2]

MS (ESI): mass calcd. for C$_{16}$H$_{19}$FN$_4$, 286.4; m/z found, 287.4 [M+H]$^+$. $^1$H NMR (DMSO-d$_6$): 9.59 (s, 2H), 7.64 (dd, J=8.8, 5.5, 2H), 7.37 (t, J=8.9, 2H), 4.10 (t, J=4.3, 2H), 3.65 (q, J=7.0, 2H), 3.43-3.37 (m, 2H), 3.10 (s, 3H), 2.98 (t, J=6.4, 2H), 1.10 (t, J=7.0, 3H).

Example 45

4-(4-Fluoro-phenyl)-2-(3-methyl-morpholin-4-yl)-5,6,7,8-tetrahydro-pyrido[4,3-d]pyrimidine

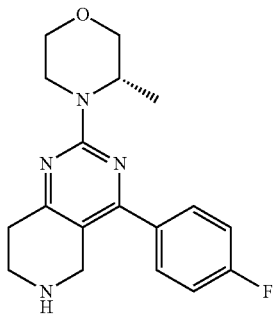 [SMILES: C[C@H]1COCCN1c1nc2c(c(-c3ccc(F)cc3)n1)CNCC2]

HPLC: $R_t$=8.4 min. MS (ESI): mass calcd. for $C_{18}H_{21}FN_4O$, 341.41; m/z found, 329.2 $[M+H]^+$.

Example 46

[4-(4-Chloro-phenyl)-5,6,7,8-tetrahydro-pyrido[4,3-d]pyrimidin-2-yl]-diethyl-amine hydrochloride

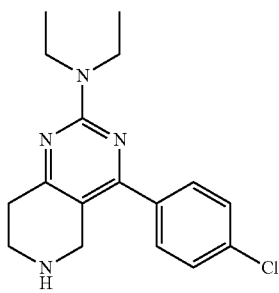 [SMILES: CCN(CC)c1nc2c(c(-c3ccc(Cl)cc3)n1)CNCC2]

HPLC: $R_t$=9.7 min. MS (ESI): mass calcd. for $C_{17}H_{21}ClN_4$, 316.8; m/z found, 317.4 $[M+H]^+$. $^1$H NMR (DMSO-$d_6$): 9.57 (s, 2H), 7.60 (m, 4H), 4.12-4.04 (m, 2H), 3.6 (q, J=6.9, 4H), 3.43-3.36 (m, 2H), 2.97 (dd, J=6.3, 2H), 1.13 (t, J=6.9, 6H).

Example 47

2-Pyrrolidin-1-yl-4-p-tolyl-5,6,7,8-tetrahydro-pyrido[4,3-d]pyrimidine

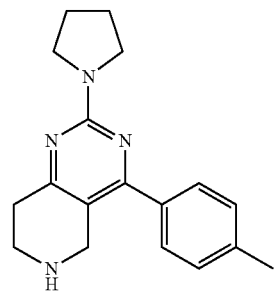 [SMILES: Cc1ccc(-c2nc(N3CCCC3)nc3c2CNCC3)cc1]

Step A: 2-Pyrrolidin-1-yl-4-p-tolyl-7,8-dihydro-5H-pyrido[4,3-d]pyrimidine-6-carboxylic acid tert-butyl ester To a mixture of 3-(4-Methyl-benzoyl)-4-oxo-piperidine-1-carboxylic acid tert-butyl ester (0.24 g, 0.74 mmol) and pyrrolidine-1-carboxamidine trifluoroacetate (0.14 g, 0.58 mmol) in t-BuOH (7.5 mL) was added sodium tert-butoxide (0.10 g, 1.1 mmol). The mixture was heated at reflux for 2 h, then cooled to rt, diluted with $H_2O$ and extracted with $CH_2Cl_2$ (2×). The combined organic extracts were dried and concentrated. The residue was purified by FCC to give the title compound (0.084 g, 29%) as a clear oil. MS (ESI): mass calcd. for $C_{23}H_{30}N_4O_2$, 394.5; m/z found, 395.5 $[M+H]^+$.

Step B: 2-Pyrrolidin-1-yl-4-p-tolyl-5,6,7,8-tetrahydro-pyrido[4,3-d]pyrimidine

To a solution of 2-Pyrrolidin-1-yl-4-p-tolyl-7,8-dihydro-5H-pyrido[4,3-d]pyrimidine-6-carboxylic acid tert-butyl ester (0.075 g, 0.19 mmol) in $CH_2Cl_2$ (3 mL) was added TFA (3 mL). After 16 h, the mixture was concentrated, diluted with saturated (satd.) aqueous (aq.) $NaHCO_3$, and extracted with $CH_2Cl_2$. The combined organic layers were dried and concentrated. Purification by FCC (2 M $NH_3$ in MeOH/$CH_2Cl_2$) provided the title compound (0.044 g, 79%). HPLC: $R_t$=7.7 min. MS (ESI): mass calcd. for $C_{18}H_{22}N_4$, 294.4; m/z found, 295.4 $[M+H]^+$. $^1$H NMR (CDCl$_3$): 7.42-7.34 (m, 2H), 7.28-7.22 (m, 2H), 3.87 (s, 2H), 3.61-3.58 (m, 4H), 3.20 (t, J=6.2, 2H), 2.82 (t, J=6.2, 2H), 2.39 (s, 3H), 1.97-1.94 (m, 4H).

Example 48

Ethyl-(4-p-tolyl-5,6,7,8-tetrahydro-pyrido[4,3-d]pyrimidin-2-yl)-amine

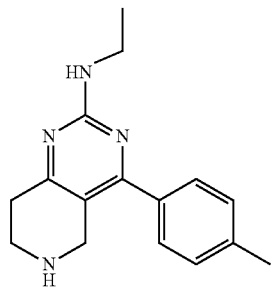 [SMILES: CCNc1nc2c(c(-c3ccc(C)cc3)n1)CNCC2]

HPLC: $R_t$=6.7 min. MS (ESI): mass calcd. for $C_{16}H_{20}N_4$, 268.4; m/z found, 269.4 $[M+H]^+$.

Example 49

2-Morpholin-4-yl-4-p-tolyl-5,6,7,8-tetrahydro-pyrido[4,3-d]pyrimidine

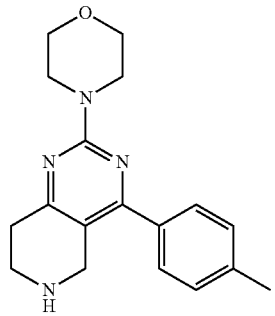 [SMILES: Cc1ccc(-c2nc(N3CCOCC3)nc3c2CNCC3)cc1]

HPLC: $R_t$=8.4 min. MS (ESI): mass calcd. for $C_{18}H_{22}N_4O$, 310.4; m/z found, 311.5 $[M+H]^+$. $^1$H NMR (CDCl$_3$): 7.43 (d, J=8.1, 2H), 7.24 (d, J=7.9, 2H), 3.95-3.97 (m, 2H), 3.82-3.75 (m, 8H), 3.28-3.15 (m, 2H), 2.86-2.75 (m, 2H), 2.40 (s, 3H).

Example 50

2-Piperidin-1-yl-4-p-tolyl-5,6,7,8-tetrahydro-pyrido[4,3-d]pyrimidine

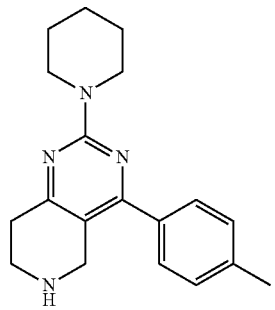 [SMILES: Cc1ccc(-c2nc(N3CCCCC3)nc3c2CNCC3)cc1]

HPLC: $R_t$=9.4 min. MS (ESI): mass calcd. for $C_{19}H_{24}N_4$, 308.4; m/z found, 309.5 $[M+H]^+$. $^1$H NMR (CDCl$_3$): 7.44 (d, J=8.1, 2H), 7.9 (d, J=7.9, 2H), 3.88 (S, 2H), 3.81-3.78 (m, 4H), 3.19 (t, J=6.2, 2H), 2.79 (t, J=6.2, 2H), 2.40 (S, 3H), 1.67-1.53 (m, 6H).

Example 51

Benzyl-(4-p-tolyl-5,6,7,8-tetrahydro-pyrido[4,3-d]pyrimidin-2-yl)-amine

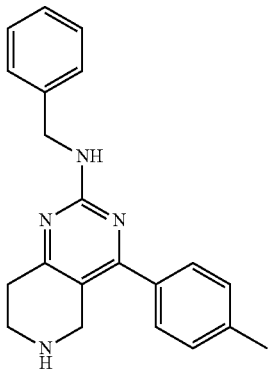 [SMILES: Cc1ccc(-c2nc(NCc3ccccc3)nc3c2CNCC3)cc1]

MS (ESI): mass calcd. for $C_{21}H_{22}N_4$, 330.4; m/z found, 331.4 [M+H]+. 1H NMR (CDCl3): 7.40-7.36 (m, 4H), 7.33-7.30 (m, 2H), 7.25-7.22 (m, 3H), 5.29 (t, J=5.7, 1H), 4.67 (d, J=5.9, 2H), 3.88 (s, 2H), 3.20 (t, J=6.1, 2H), 2.81 (t, J=6.1, 2H), 2.4 (s, 3H).

Example 52

6-Methyl-2-pyrrolidin-1-yl-4-p-tolyl-5,6,7,8-tetrahydro-pyrido[4,3-d]pyrimidine

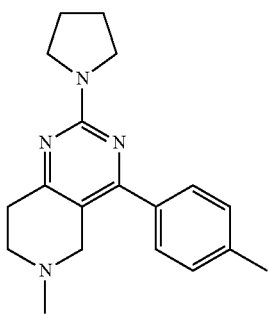 [SMILES: Cc1ccc(-c2nc(N3CCCC3)nc3c2CN(C)CC3)cc1]

To a solution of 2-pyrrolidin-1-yl-4-p-tolyl-5,6,7,8-tetrahydro-pyrido[4,3-d]pyrimidine (0.034 g, 0.12 mmol) in MeOH (2 mL) was added formaldehyde (37% in water; 0.10 mL) and NaBH(OAc)3 (0.030 g, 0.14 mmol). After the reaction was judged complete, the mixture was diluted with 1 N NaOH and extracted with CH2Cl2 (3×). The combined organic layers were dried and concentrated. The resulting residue was purified by FCC (2 M NH3 in MeOH/CH2Cl2) to give 0.033 g (91%) of the title compound. HPLC: $R_t$=8.2 min. MS (ESI): mass calcd. for $C_{19}H_{24}N_4$, 308.4; m/z found, 309.5 [M+H]+. 1H NMR (CDCl3): 7.44 (d, J=8.1, 2H), 7.24 (d, J=7.9, 2H), 3.61-3.58 (m, 4H), 3.42 (5, 2H), 2.92 (dd, J=6.1, 6.0, 2H), 2.74 (dd, J=6.1, 6.0, 2H), 2.40 (5, 3H), 2.39 (5, 3H), 1.97-1.94 (m, 4H).

The compounds in Examples 53-60 were prepare using methods analogous to those described in the preceding examples.

Example 53

4-(4-Chloro-phenyl)-2-(2-methyl-pyrrolidin-1-yl)-6,7,8,9-tetrahydro-5H-1,3,6-triaza-benzocycloheptene

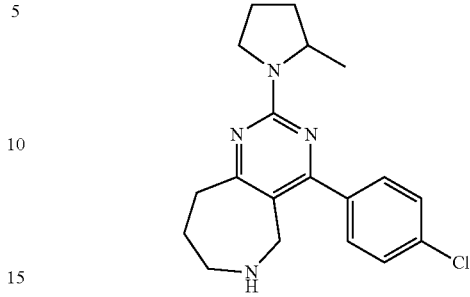

HPLC: $R_t$=6.1 min. MS (ESI): mass calcd. for $C_{19}H_{23}ClN_4$, 342.9; m/z found, 343.4 [M+H]+. 1H NMR (CDCl3): 7.48 (d, J=8.5, 2H), 7.39 (d, J=8.5, 2H), 4.33-4.28 (m, 1H), 3.82 (s, 2H), 3.66-3.56 (m, 2H), 3.20-3.18 (m, 2H), 3.02-3.00 (m, 2H), 2.09-1.98 (m, 2H), 1.92-1.87 (m, 1H), 1.84-1.79 (m, 2H), 1.70-1.66 (m, 1H), 1.26 (d, J=6.3, 3H).

Example 54

4-(4-Chloro-phenyl)-2-(2-methyl-pyrrolidin-1-yl)-6,7,8,9-tetrahydro-5H-pyrimido[4,5-d]azepine

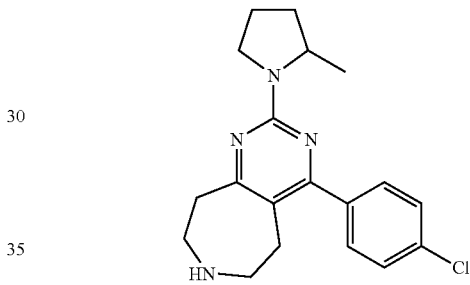

HPLC: $R_t$=9.0 min. MS (ESI): mass calcd. for $C_{19}H_{23}ClN_4$, 342.9; m/z found, 343.3 [M+H]+. 1H NMR (CDCl3): 7.40-7.39 (m, 4H), 4.31-4.26 (m, 1H), 3.66-3.62 (m, 1H), 3.59-3.55 (m, 1H), 3.08-3.02 (m, 4H), 2.96-2.86 (m, 2H), 2.81-2.78 (m, 2H), 2.10-1.98 (m, 2H), 1.92-1.87 (m, 1H), 1.71-1.66 (m, 1H), 1.26 (d, J=6.3 Hz, 3H).

Example 55

Benzyl-[4-(4-chloro-phenyl)-6,7,8,9-tetrahydro-5H-1,3,6-triaza-benzocyclohepten-2-yl]-amine

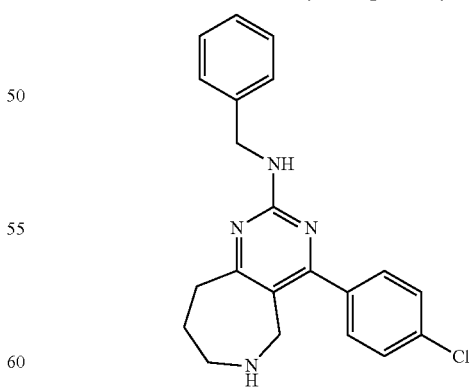

HPLC: $R_t$=9.7 min. MS (ESI): mass calcd. for $C_{21}H_{21}ClN_4$, 364.9; m/z found, 365.3 [M+H]+. 1H NMR (CDCl3): 7.44-7.42 (m, 2H), 7.40-7.37 (m, 2H), 7.36-7.30 (m, 4H), 7.27-7.25 (m, 1H), 5.36 (t, J=5.9, 1H), 4.66 (d, J=6.0, 2H), 3.84 (s, 2H), 3.20-3.18 (m, 2H), 3.02-2.99 (m, 2H), 1.85-1.80 (m, 2H).

Example 56

Benzyl-[4-(4-chloro-phenyl)-6,7,8,9-tetrahydro-5H-pyrimido[4,5-d]azepin-2-yl]-amine

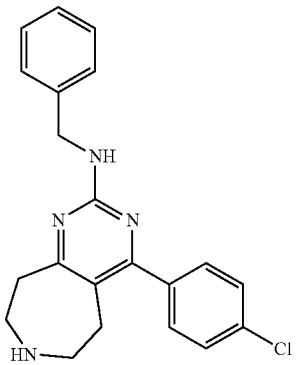 [SMILES: Clc1ccc(-c2nc(NCc3ccccc3)nc3c2CCNCC3)cc1]

HPLC: $R_t$=9.6 min. MS (ESI): mass calcd. for $C_{21}H_{21}ClN_4$, 364.9; m/z found, 365.3 [M+H]$^+$.

Example 57

4-(4-Chloro-phenyl)-2-morpholin-4-yl-6,7,8,9-tetrahydro-5H-1,3,6-triaza-benzocycloheptene

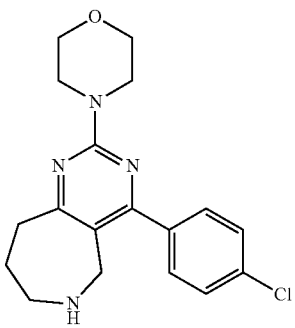 [SMILES: Clc1ccc(-c2nc(N3CCOCC3)nc3c2CNCCC3)cc1]

HPLC: $R_t$=8.9 min. MS (ESI): mass calcd. for $C_{18}H_{21}ClN_4O$, 344.8; m/z found, 345.2 [M+H]$^+$. $^1$H NMR (CDCl$_3$): 7.47 (d, J=8.5, 2H), 7.39 (d, J=8.5, 2H), 3.84-3.80 (m, 6H), 3.77-3.74 (m, 4H), 3.21-3.18 (m, 2H), 3.04-2.99 (m, 2H), 1.85-1.78 (m, 2H).

Example 58

4-(4-Chloro-phenyl)-2-morpholin-4-yl-6,7,8,9-tetrahydro-5H-pyrimido[4,5-d]azepine

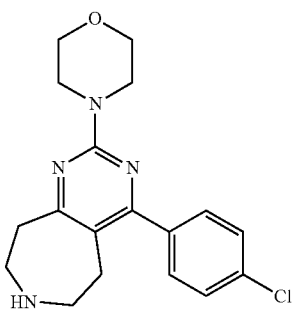 [SMILES: Clc1ccc(-c2nc(N3CCOCC3)nc3c2CCNCC3)cc1]

HPLC: $R_t$=8.9 min. MS (ESI): mass calcd. for $C_{18}H_{21}ClN_4O$, 344.8; m/z found, 345.2 [M+H]$^+$. $^1$H NMR (CDCl$_3$): 7.42-7.37 (m, 4H), 3.82-3.74 (m, 8H), 3.07-3.00 (m, 4H), 2.92-2.85 (m, 2H), 2.82-2.76 (m, 2H).

Example 59

[4-(4-Chloro-phenyl)-6,7,8,9-tetrahydro-5H-1,3,6-triaza-benzocyclohepten-2-yl]-diethyl-amine hydrochloride

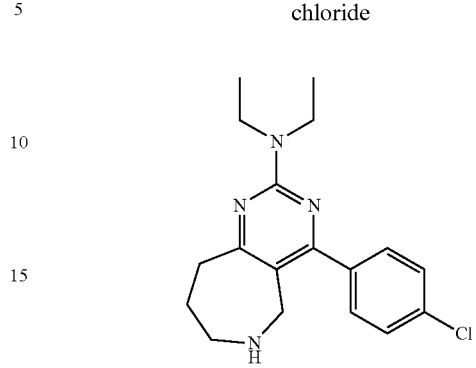

HPLC: $R_t$=10.0 min. MS (ESI): mass calcd. for $C_{18}H_{23}ClN_4$, 330.9; m/z found, 331.4 [M+H]$^+$. $^1$H NMR (DMSO-d$_6$): 9.53-9.17 (m, 2H), 7.62-7.57 (m, 4H), 4.08-4.06 (m, 2H), 3.68-3.56 (m, 4H), 3.36-3.30 (m, 2H), 3.04-3.02 (m, 2H), 1.97-1.92 (m, 2H), 1.13 (t, J=6.9, 6H).

Example 60

[4-(4-Chloro-phenyl)-6,7,8,9-tetrahydro-5H-pyrimido[4,5-d]azepin-2-yl]-diethyl-amine

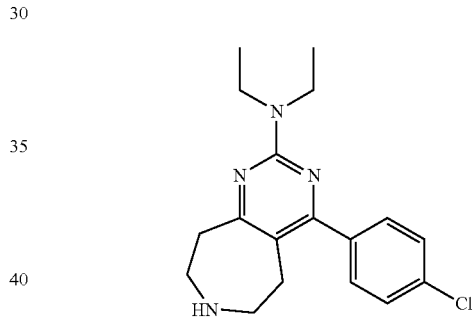

HPLC: $R_t$=9.6 min. MS (ESI): mass calcd. for $C_{18}H_{23}ClN_4$, 330.9; m/z found, 331.4 [M+H]$^+$. $^1$H NMR (CDCl$_3$): 7.43-7.38 (m, 4H), 3.64 (q, J=7.0, 4H), 3.06-2.99 (m, 4H), 2.92-2.86 (m, 2H), 2.81-2.73 (m, 2H), 1.18 (t, J=7.0, 6H).

Example 61

Dimethyl-(4-p-tolyl-5,6,7,8-tetrahydro-pyrido[4,3-d]pyrimidin-2-yl)-amine

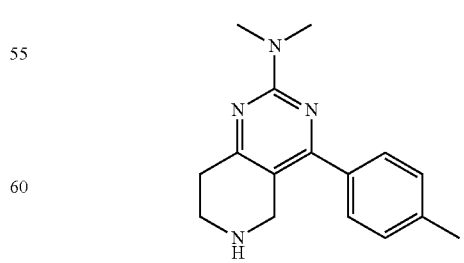

MS (ESI): mass calcd. for $C_{16}H_{20}N_4$, 294.4; m/z found, 269.4 [M+H]$^+$. $^1$H NMR (CDCl$_3$): 7.45-7.44 (m, 2H), 7.24-7.23 (m, 2H), 3.88 (s, 2H), 3.21-3.19 (m, 8H), 2.81 (t, J=6.2, 2H), 2.40 (s, 3H).

Example 64

2-(1,1-Dioxo-1λ⁶-thiomorpholin-4-yl)-4-p-tolyl-6,7,8,9-tetrahydro-5H-pyrimido[4,5-d]azepine

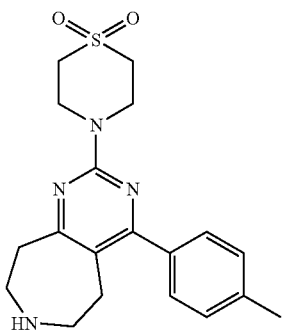 [SMILES: Cc1ccc(-c2nc(N3CCS(=O)(=O)CC3)nc3c2CCNCC3)cc1]

Step A: (tert-Butoxycarbonylimino-thiomorpholin-4-yl-methyl)-carbamic acid tert-butyl ester A solution of [[[(1,1-dimethylethoxy)carbonyl]amino]-(methylthio)methylene]-carbamic acid, 1,1-dimethylethyl ester [CAS 107819-90-9] (21 g, 0.0723 mol) in DMF (450 mL) was treated sequentially with thiomorpholine (7 mL, 0.0723 mol), mercury chloride (19.6 g, 0.0723 mol), and Et₃N (30 mL, 0.22 mol) and the reaction mixture was stirred for 18 h. The mixture was diluted with EtOAc and filtered through a pad of diatomaceous earth. The filtrate was concentrated, diluted with water and EtOAc and filtered again through a pad of diatomaceous earth. The filtrate aqueous layer was separated and extracted with EtOAc (2×). The combined organic layers were washed with water, then satd. aq. NaCl, dried, and concentrated. The solid was triturated with 20% Et₂O/40-60° C. petrol. The solid was filtered off and was washed with 20% Et₂O/40-60° C. petrol followed by 40-60° C. petrol. The solid was dried under vacuum to give 21.2 g (85%) as a white solid. Note: The reaction was performed with a trap for gaseous loss of methanethiol.

Step B: Thiomorpholine-4-carboxamidine

Trifluoroacetic acid (50 mL, 0.073 mol) was added dropwise to a stirred mixture of (tert-Butoxycarbonylimino-thiomorpholin-4-yl-methyl)-carbamic acid tert-butyl ester (21 g, 0.0723 mol) in DCM (200 mL) and water (10 mL). After 3 days at rt, the solvent was evaporated and re-evaporated with 2-propanol. The resulting semi-solid was triturated with 10% 2-propanol/Et₂O. The solid was filtered off and was washed with 10% 2-propanol/Et₂O and then with Et₂O. The product was dried in vacuo over phosphoric oxide, to give 15.72 g as a white solid.

Step C: 4-Hydroxy-2-thiomorpholin-4-yl-5,6,8,9-tetrahydro-pyrimido[4,5-d]azepine-7-carboxylic acid tert-butyl ester A mixture of 1H-azepine-1,4-dicarboxylic acid, hexahydro-5-oxo-, 1-(1,1-dimethylethyl) 4-ethyl ester [CAS 141642-82-2] (17.1 g, 0.062 mol; 95+%) in EtOH (250 mL) was treated with thiomorpholine-4-carboxamidine (15.6 g, 0.060 mol), followed by EtONa (2.67 M in EtOH, 60 mL). After 18 h at 85-90° C., the mixture was cooled and the solvent was evaporated. The crude residue was diluted with DCM and water and filtered. The solid was washed with water and dried under vacuum to give 1.5 g of the title compound as a white solid. The filtrate layers were separated and the organic layer was dried (MgSO₄). On standing overnight a precipitate formed in the organic extract. This precipitate was collected by filtration, washed with water and dried under vacuum to give an additional portion of the title compound. The aqueous layer was exhaustively extracted with EtOAc. The combined organic extracts were dried (MgSO₄) and concentrated to give an additional portion of the title compound. All portions were combined to give 5.0 g of the title compound.

Step D: 2-(1,1-Dioxo-1λ⁶-thiomorpholin-4-yl)-4-hydroxy-5,6,8,9-tetrahydro-pyrimido[4,5-d]azepine-7-carboxylic acid tert-butyl ester.

A <4° C. solution of 4-hydroxy-2-thiomorpholin-4-yl-5,6,8,9-tetrahydro-pyrimido[4,5-d]azepine-7-carboxylic acid tert-butyl ester (1.5 g, 0.0041 mol) in DCM (200 mL) was treated portionwise with m-chloroperbenzoic acid (mCPBA, 77%; 2.8 g, 0.0122 mol). The resulting mixture was stirred for 1 h at <4° C. and then at rt for 18 h. The mixture was diluted with DCM and washed with 10% aq. NaHSO₃ and then with 10% aq. Na₂CO₃. The organic layer was dried (MgSO₄) and concentrated to give 1.6 g of the title compound as a pale yellow solid. The solid was a mixture (71% product) but was used as such in the next reaction.

Step E: 2-(1,1-Dioxo-1λ⁶-thiomorpholin-4-yl)-4 trifluoromethanesulfonyloxy-5,6,8,9-tetrahydro-pyrimido[4,5-d]azepine-7-carboxylic acid tert-butyl ester A 0° C. solution of 2-(1,1-dioxo-1λ⁶-thiomorpholin-4-yl)-4-hydroxy-5,6,8,9-tetrahydro-pyrimido[4,5-d]azepine-7-carboxylic acid tert-butyl ester (1.6 g, crude mixture) and Et₃N (1.7 mL, 0.012 mol) in DCM (25 mL) was treated with trifluoromethanesulfonic acid anhydride (1.00 mL, 0.006 mol, 99+%) dropwise over 10 min. The resulting mixture was stirred at 0° C. or lower for 1 h. Ice-cold water (100 mL) was added rapidly dropwise and the phases were separated. The aqueous phase was extracted with DCM (3×50 mL). The separated organic layers were combined, dried, and presorbed onto flash silica gel. The product was purified by FCC (EtOAc/40-60° C. petrol). The desired fractions were collected and concentrated to give 1.05 g of the title compound as a pale yellow solid.

Step F: 2-(1,1-Dioxo-1λ⁶-thiomorpholin-4-yl)-4-p-tolyl-6,7,8,9-tetrahydro-5H-pyrimido[4,5-d]azepine A mixture of 2-(1,1-dioxo-1λ⁶-thiomorpholin-4-yl)-4 trifluoromethanesulfonyloxy-5,6,8,9-tetrahydro-pyrimido[4,5-d]azepine-7-carboxylic acid tert-butyl ester (0.0008 mol), (4-methylphenyl)-boronic acid (0.0008 mol), Pd(dppf)Cl₂ (0.00008 mol) and K₂CO₃ (0.0016 mol) in 2-propanone/toluene/water (4:4:1, 8 mL) was stirred in a microwave for 30 min at 130° C. The separated organic layer was filtered over silica gel and the filtrate was concentrated. The residue was purified by FCC (petroleum ether/Et₂O). The product fractions were collected and the solvent was evaporated. This residue was dissolved in TFA/DCM/water (5:12:1, 12 mL) and stirred at rt for 90 min. The mixture was concentrated and residue was diluted with 1 M NaOH and extracted with DCM (2×). The combined organic layers were washed with satd. NaCl, dried, and concentrated. The residue was recrystallized from 2-propanol to give 0.190 g (64%) of the title compound.

Example 65

2-(1,1-Dioxo-1λ⁶-thiomorpholin-4-yl)-7-methyl-4-p-tolyl-6,7,8,9-tetrahydro-5H-pyrimido[4,5-d]azepine

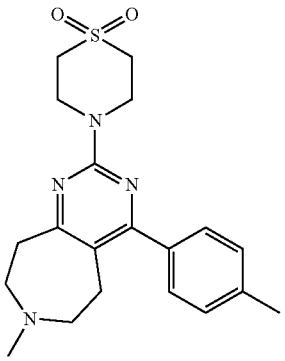 [SMILES: Cc1ccc(-c2nc(N3CCS(=O)(=O)CC3)nc3c2CCN(C)CC3)cc1]

A mixture of 2-(1,1-dioxo-1λ⁶-thiomorpholin-4-yl)-4-p-tolyl-6,7,8,9-tetrahydro-5H-pyrimido[4,5-d]azepine (0.060 g, 0.00016 mol), iodomethane (0.015 mL, 0.00016 mol) and N-ethyl-N-(1-methylethyl)-2-propanamine (0.056 mL, 0.00032 mol) in DCM (2 mL) was stirred at rt for 3 h. The mixture was diluted with DCM and washed with water (3×) and satd. aq. NaCl. The separated organic layer was dried and concentrated. The residue was purified by FCC [7 N NH₃/MeOH/DCM] to give 0.010 g (16%) of the title compound.

The compounds in Examples 66-103 were prepared from 4-oxo-piperidine-1-carboxylic acid tert-butyl ester using methods analogous to those described in Example 1.

| Ex. | Structure | Chemical Name |
|---|---|---|
| 66 | 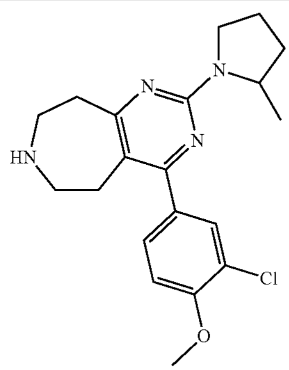 [SMILES: COc1ccc(-c2nc(N3CCCC3C)nc3c2CCNCC3)cc1Cl] | 4-(3-chloro-4-methoxyphenyl)-6,7,8,9-tetrahydro-2-(2-methyl-1-pyrrolidinyl)-5H-pyrimido[4,5-d]azepine |
| 67 | 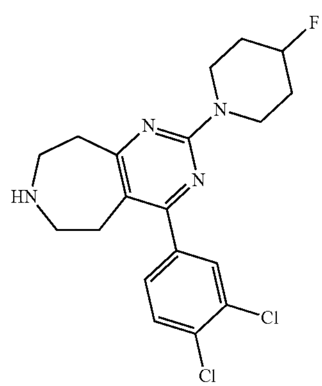 [SMILES: FC1CCN(c2nc3c(c(-c4ccc(Cl)c(Cl)c4)n2)CCNCC3)CC1] | 4-(3,4-dichlorophenyl)-2-(4-fluoro-1-piperidinyl)-6,7,8,9-tetrahydro-5H-pyrimido[4,5-d]azepine |
| 68 | 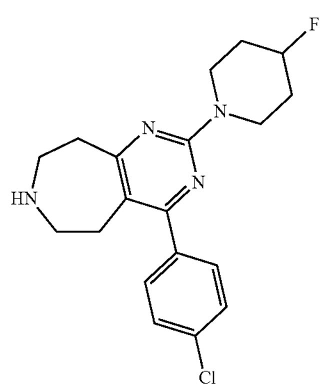 [SMILES: FC1CCN(c2nc3c(c(-c4ccc(Cl)cc4)n2)CCNCC3)CC1] | 4-(4-chlorophenyl)-2-(4-(fuoro-1-piperidinyl)-6,7,8,9-tetrahydro-5H-pyrimido[4,5-d]azepine |

-continued

| Ex. | Structure | Chemical Name |
|---|---|---|
| 69 | 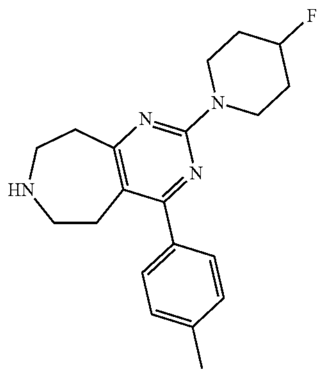 [SMILES: Cc1ccc(-c2nc(N3CCC(F)CC3)nc3c2CCNCC3)cc1] | 2-(4-fluoro-1-piperidinyl)-6,7,8,9-tetrahydro-4-(4-methylphenyl)-5H-pyrimido[4,5-d]azepine |
| 70 | 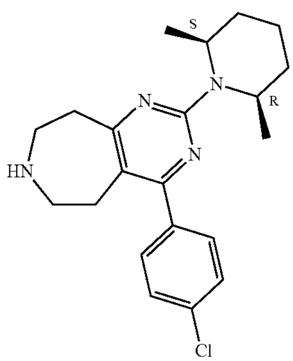 | 4-(4-chlorophenyl)-2-[(2R,6S)-2,6-dimethyl-1-piperidinyl]-6,7,8,9-tetrahydro-5H-pyrimido[4,5-d]azepine |
| 71 | 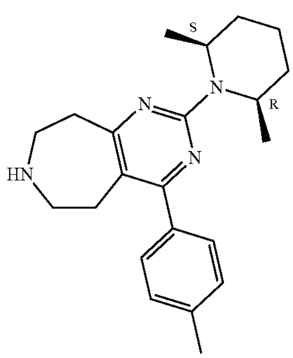 | 2-[(2R,6S)-2,6-dimethyl-1-piperidinyl]-6,7,8,9-tetrahydro-4-(4-methylphenyl)-5H-pyrimido[4,5-d]azepine |
| 72 | 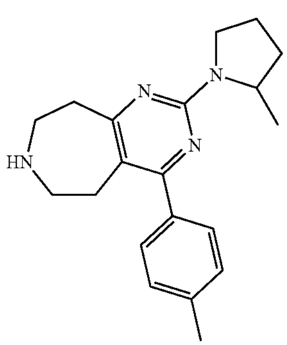 [SMILES: Cc1ccc(-c2nc(N3CCCC3C)nc3c2CCNCC3)cc1] | 6,7,8,9-tetrahydro-4-(4-methylphenyl)-2-(2-methyl-1-pyrrolidinyl)-5H-pyrimido[4,5-d]azepine |

| Ex. | Structure | Chemical Name |
|---|---|---|
| 73 | 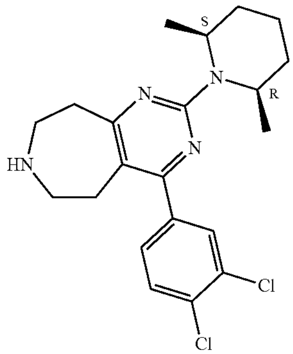 | 4-(3,4-dichlorophenyl)-2-[(2R,6S)-2,6-dimethyl-1-piperidinyl]-6,7,8,9-tetrahydro-5H-pyrimido[4,5-d]azepine |
| 74 | 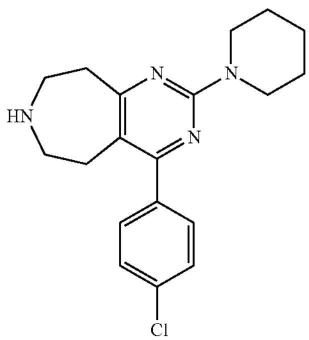 [SMILES: Clc1ccc(-c2nc(N3CCCCC3)nc3c2CCNCC3)cc1] | 4-(4-chlorophenyl)-6,7,8,9-tetrahydro-2-(1-piperidinyl)-5H-pyrimido[4,5-d]azepine |
| 75 | 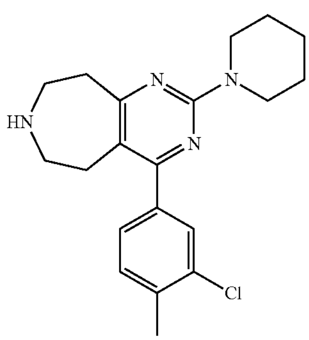 [SMILES: Cc1ccc(-c2nc(N3CCCCC3)nc3c2CCNCC3)cc1Cl] | 4-(3-chloro-4-methylphenyl)-6,7,8,9-tetrahydro-2-(1-piperidinyl)-5H-pyrimido[4,5-d]azepine |
| 76 | 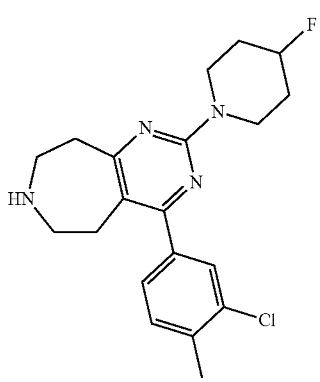 [SMILES: Cc1ccc(-c2nc(N3CCC(F)CC3)nc3c2CCNCC3)cc1Cl] | 4-(3-chloro-4-methylphenyl)-2-(4-fluoro-1-piperidinyl)-6,7,8,9-tetrahydro-5H-pyrimido[4,5-d]azepine |

| Ex. | Structure | Chemical Name |
|---|---|---|
| 77 | 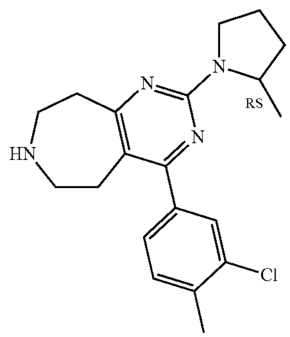 [SMILES: Cc1ccc(-c2nc(N3CCCC3C)nc3c2CCNCC3)cc1Cl] | 4-(3-chloro-4-methylphenyl)-6,7,8,9-tetrahydro-2-(2-methyl-1-pyrrolidinyl)-5H-pyrimido[4,5-d]azepine |
| 78 | 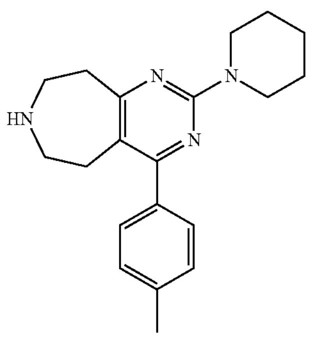 [SMILES: Cc1ccc(-c2nc(N3CCCCC3)nc3c2CCNCC3)cc1] | 6,7(8,9-tetrahydro-4-t4-methylphenyl)-2-(1-piperidinyl)-5H-pyrimido[4,5-d)azepine |
| 79 | 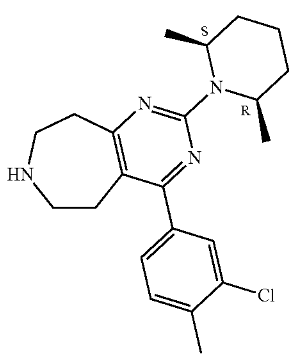 | 4-(3-chloro-4-methylphenyl)-2-[(2R,6S)-2,6-dimethyl-1-piperidinyl]-6,7,8,9-tetrahydro-5H-pyrimido[4,5-d]azepine |
| 80 | 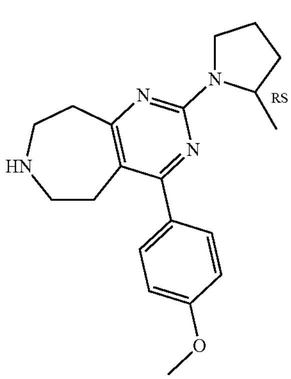 [SMILES: COc1ccc(-c2nc(N3CCCC3C)nc3c2CCNCC3)cc1] | 6,7,8,9-tetrahydro-4-(4-methoxyphenyl)-2-(2-methyl-1-pyrrolidinyl)-5H-pyrimido[4,5-d]azepine |

| Ex. | Structure | Chemical Name |
|---|---|---|
| 81 | 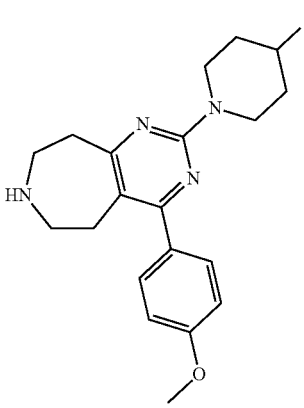 | 2-(4-fluoro-1-piperidinyl)-6,7,8,9-tetrahydro-4-(4-methoxyphenyl)-5H-pyrimido[4,5-d]azepine |
| 82 | 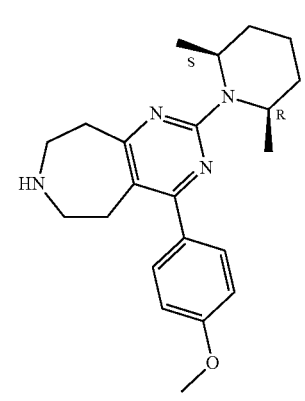 | 2-[(2R,6S)-2,6-dimethyl-1-piperidinyl]-6,7,8,9-tetrahydro-4-(4-methoxyphenyl)-5H-pyrimido[4,5-d]azepine |
| 83 | 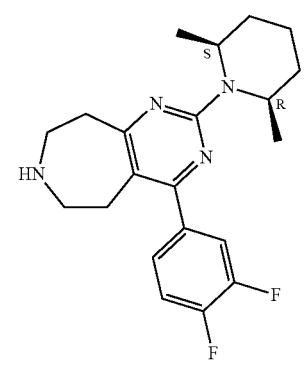 | 4-(3,4-difluorophenyl)-2-[(2R,6S)-2,6-dimethyl-1-piperidinyl]-6,7,8,9-tetrahydro-5H-pyrimido[4,5-d]azepine |
| 84 | 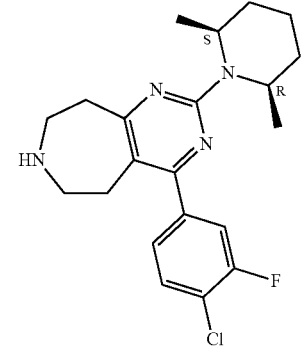 | 4-(4-chloro-3-fluorophenyl)-2-[(2R,6S)-2,6-dimethyl-1-piperidinyl]-6,7,8,9-tetrahydro-5H-pyrimido[4,5-d]azepine |

| Ex. | Structure | Chemical Name |
|---|---|---|
| 85 | 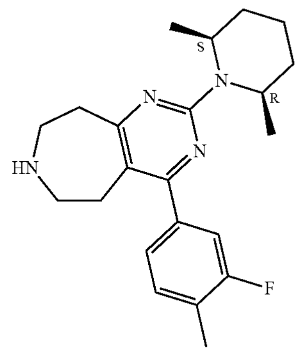 | 2-[(2R,6S)-2,6-dimethyl-1-piperidinyl]-4-(3-fluoro-4-methylphenyl)-6,7,8,9-tetrahydro-5H-pyrimido[4,5-d]azepine |
| 86 | 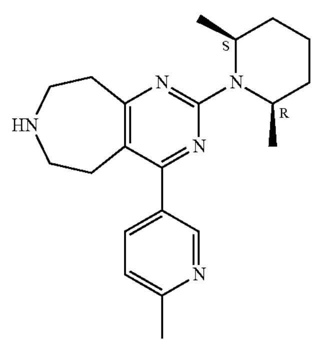 | 2-[(2R,6S)-2,6-dimethyl-1-piperidinyl]-6,7,8,9-tetrahydro-4-(6-methyl-3-pyridinyl)-5H-pyrimido[4,5-d]azepine |
| 87 | 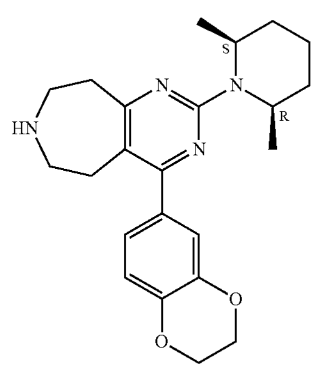 | 4-(2,3-dihydro-1,4-benzodioxin-6-yl)-2-[(2R,6S)-2,6-dimethyl-1-piperidinyl]-6,7,8,9-tetrahydro-5H-pyrimido[4,5-d]azepine |
| 88 | 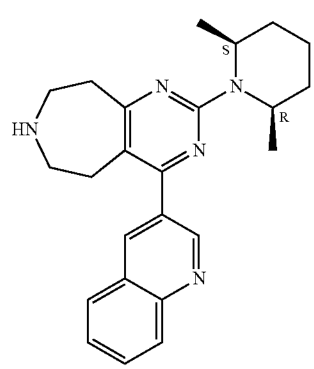 | 2-[(2R(6S)-2,6-dimethyl-1-piperidinyl]-6,7,8,9-tetrahydro-4-(3-quinolinyl)-5H-pyrimido[4,5-d]azepine |

| Ex. | Structure | Chemical Name |
|---|---|---|
| 89 | 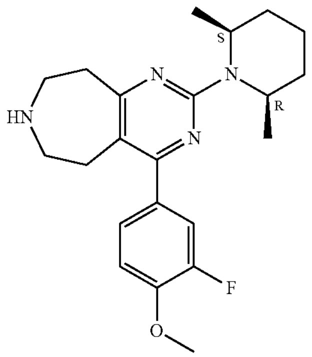 | 2-[(2R,6S)-2,6-dimethyl-1-piperidinyl]-4-(3-fluoro-4-methoxyphenyl)-6,7,8,9-tetrahydro-5H-pyrimido[4,5-d]azepine |
| 90 | 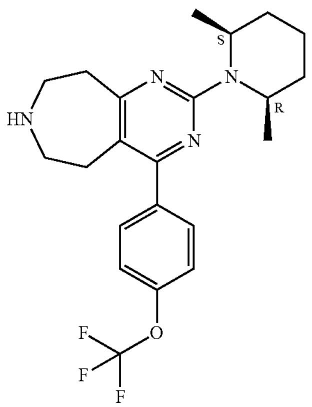 | 2-[(2R,6S)-2,6-dimethyl-1-piperidinyl]-6,7,8,9-tetrahydro-4-[4-(trifluoromethoxy)phenyl]-5H-pyrimido[4,5-d]azepine |
| 91 | 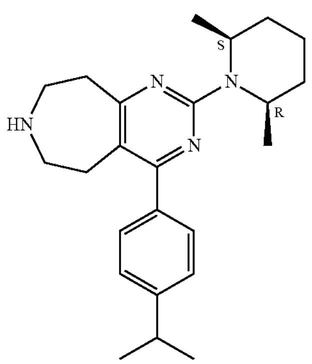 | 2-[(2R,6S)-2,6-dimethyl-1-piperidinyl]-6,7,8,9-tetrahydro-4-[4-(1-methylethyl)phenyl]-5H-pyrimido[4,5-d]azepine |
| 92 | 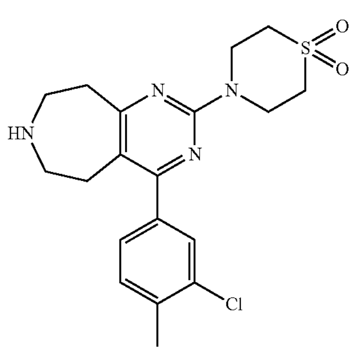 [SMILES: Cc1ccc(-c2nc(N3CCS(=O)(=O)CC3)nc3c2CCNCC3)cc1Cl] | 4-(3-Chloro-4-methyl-phenyl)-2-(1,1-dioxo-1$\lambda^6$-thiomorpholin-4-yl)-6,7,8,9-tetrahydro-5H-pyrimido[4,5-d]azepine |

| Ex. | Structure | Chemical Name |
|---|---|---|
| 93 | 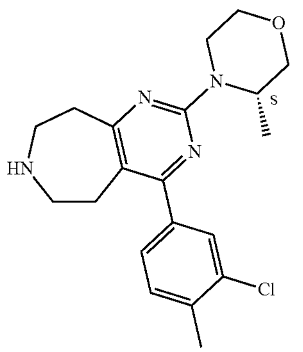 | 4-(3-chloro-4-methylphenyl)-6,7,8,9-tetrahydro-2-[(3S)-3-methyl-4-morpholinyl]-5H-pyrimido[4,5-d]azepine |
| 94 | 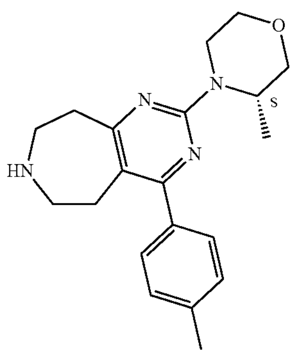 | 6,7,8,9-tetrahydro-2-[(3S)-3-methyl-4-morpholinyl]-4-(4-methylphenyl)-5H-pyrimido[4,5-d]azepine |
| 95 | 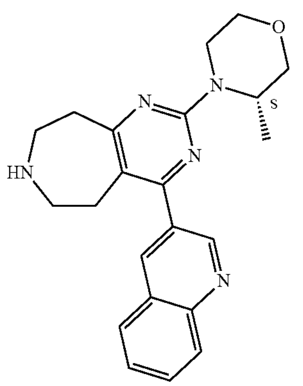 | 6,7,8,9-tetrahydro-2-[(3S)-3-methyl-4-morpholinyl]-4-(3-quinolinyl)-5H-pyrimido[4,5-d]azepine |
| 96 | 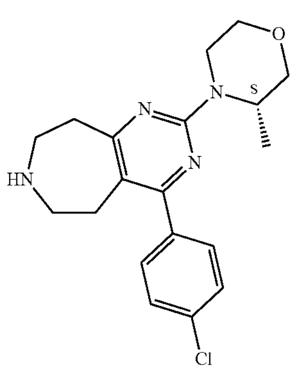 | 4-(4-chlorophenyl)-6,7,8,9-tetrahydro-2-[(3S)-3-methyl-4-morpholinyl]-5H-pyrimido[4,5-d]azepine |

-continued

| Ex. | Structure | Chemical Name |
|---|---|---|
| 97 | 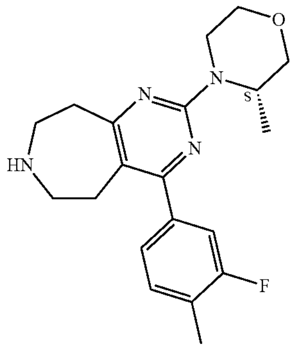 | 4-(3-fluoro-4-methylphenyl)-6,7,8,9-tetrahydro-2-[(3S)-3-methyl-4-morpholinyl]-5H-pyrimido[4,5-d]azepine |
| 98 | 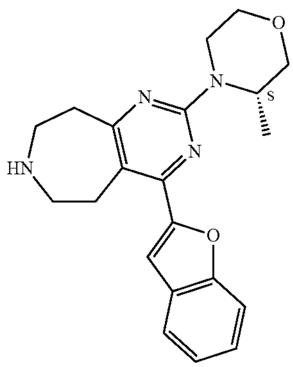 | 4-(2-benzofuranyl)-6,7,8,9-tetrahydro-2-[(3S)-3-methyl-4-morpholinyl]-5H-pyrimido[4,5-d]azepine |
| 99 | 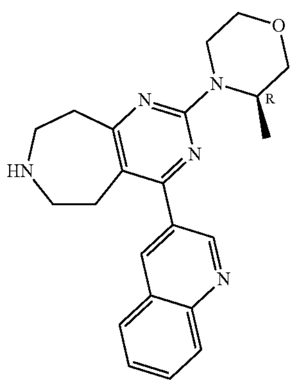 | 6,7,8,9-tetrahydro-2-[(3R)-3-methyl-4-morpholinyl]-4-(3-quinolinyl)-5H-pyrimido[4,5-d]azepine |
| 100 | 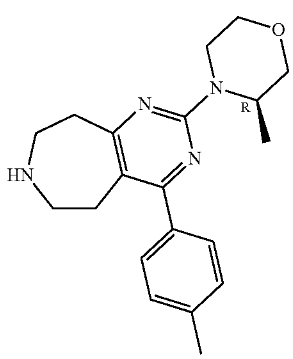 | 6,7,8,9-tetrahydro-2-[(3R)-3-methyl-4-morpholinyl]-4-(4-methylphenyl)-5H-pyrimido[4,5-d]azepine |

| Ex. | Structure | Chemical Name |
|---|---|---|
| 101 | 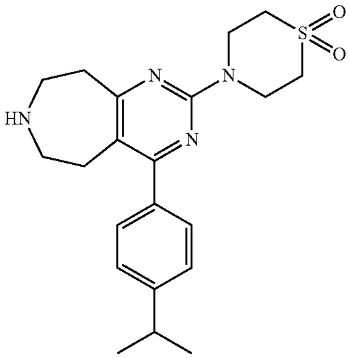 [SMILES: CC(C)c1ccc(-c2nc(N3CCS(=O)(=O)CC3)nc3c2CCNCC3)cc1] | 2-(1,1-Dioxo-1λ⁶-thiomorpholin-4-yl)-4-(4-isopropyl-phenyl)-6,7,8,9-tetrahydro-5H-pyrimido[4,5-d]azepine |
| 102 | 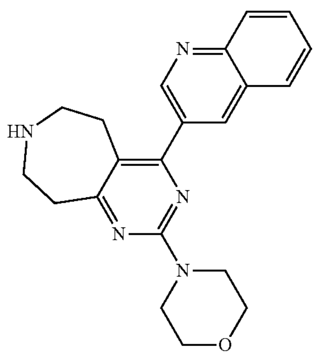 [SMILES: c1ccc2ncc(-c3nc(N4CCOCC4)nc4c3CCNCC4)cc2c1] | 2-Morpholin-4-yl-4-quinolin-3-yl-6,7,8,9-tetrahydro-5H-pyrimido[4,5-d]azepine |
| 103 | 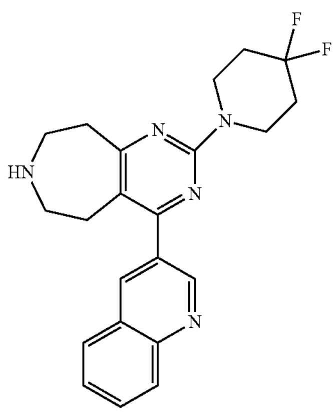 [SMILES: FC1(F)CCN(c2nc3c(c(-c4cnc5ccccc5c4)n2)CCNCC3)CC1] | 2-(4,4-difluoro-1-piperidinyl)-6,7,8,9-tetrahydro-4-(3-quinolinyl)-5H-pyrimido[4,5-d]azepine |

For LCMS-characterization of the compounds in Examples 66-103, the following methods were used.

General Procedure A

The HPLC gradient was supplied by an Agilent 1100 module comprising a pump and diode-array detector (DAD) with Gilson 215 autosampler. Flow from the column was split to a MS detector. Ionisation is either electrospray or APCI dependent on compound types. Typical electrospray conditions use a capillary needle voltage of 3.5 kV and a cone voltage of 25 V. The source temperature was maintained at a temperature between 120-150° C. (the exact temperature was determined on a compound basis). Typical APCI conditions use a corona discharge current of 17 µA and a cone voltage of 25 V. The source temperature was maintained at a temperature between 140-160° C. (the exact temperature was determined on a compound basis). The desolvation temperature was 350° C. Mass spectra were acquired by scanning from 100 to 1000, for example in 1 second using a dwell time of 0.1 sec. Nitrogen was used as the nebulizer gas.

General Procedure B

The HPLC gradient was supplied by a Waters 1512 pump with a Waters diode-array detector (DAD) with Gilson 215 autosampler. Flow from the column was split to a MS detector. Ionisation is either electrospray or APCI dependent on compound types. Typical electrospray conditions use a capillary needle voltage of 3.5 kV and a cone voltage of 25 V. The source temperature was maintained at a temperature between 120-150° C. (the exact temperature was determined on a compound basis). Typical APCI conditions use a corona discharge current of 17 µA and a cone voltage of 25 V. The source temperature was maintained at 140-160° C. (the exact temperature was determined on a compound basis). The desolvation temperature was 350° C. Mass spectra were acquired by scanning from 100 to 1000, for example in 1 second using a dwell time of 0.1 sec. Nitrogen was used as the nebulizer gas.

General Procedure C

The HPLC gradient was supplied by a HP 1100 from Agilent Technologies comprising a quaternary pump with degasser, an autosampler, a column oven (set at 40° C.) and diode-array detector (DAD). Flow from the column was split to a MS detector. The MS detector was configured with an electrospray ionization source. Nitrogen was used as the nebulizer gas. The source temperature was maintained at 140° C. Data acquisition was performed with MassLynx-Openlynx software.

Method 1

In addition to general procedure A: Reversed phase HPLC was carried out on a Phenomenex Luna 5μ C18 (2) column (4.6×100 mm; plus guard cartridge) with a flow rate of 2 ml/min. Two mobile phases (mobile phase A: water with 0.1% formic acid; mobile phase B: acetonitrile with 0.1% formic acid) were employed to run a gradient condition from 95% A to 95% B with a flow rate of 2 ml/min in 3.5 minutes and hold for 2 minutes. Typically, injection volumes of between 2 μl and 7 μl, inclusive were used.

Method 2

In addition to general procedure B: Reversed phase HPLC was carried out on a Waters Xterra MS 5μ C18 column (4.6×100 mm; plus guard cartridge) with a flow rate of 2 ml/min. Two mobile phases (mobile phase A: water with 7 mM ammonia; mobile phase B: acetonitrile with 7 mM ammonia) were employed to run a gradient condition from 95% A to 95% B with a flow rate of 2 ml/min in 3.5 minutes and hold for 2 minutes. Typically, injection volumes of between 2 μl and 7 μl, inclusive were used.

Method 3

In addition to general procedure C: Reversed phase HPLC was carried out on an ACE-C18 column (3.0 μm, 4.6×30 mm) from Advanced Chromatography Technologies, with a flow rate of 1.5 ml/min. The gradient conditions used are: 80% A (0.5 g/l ammonium acetate solution), 10% B (acetonitrile), 10% C (methanol) to 50% B and 50% C in 6.5 minutes, to 100% B at 7 minutes and equilibrated to initial conditions at 7.5 minutes until 9.0 minutes. Injection volume 5 μl. High-resolution mass spectra (Time of Flight, TOF) were acquired only in positive ionization mode by scanning from 100 to 750 in 0.5 seconds using a dwell time of 0.1 seconds. The capillary needle voltage was 2.5 kV for positive ionization mode and the cone voltage was 20 V. Leucine-Enkephaline was the standard substance used for the lock mass calibration.

Method 4

In addition to general procedure C: Reversed phase HPLC was carried out on an ACE-C18 column (3.0 μm, 4.6×30 mm) from Advanced Chromatography Technologies, with a flow rate of 1.5 ml/min. The gradient conditions used are: 80% A (0.5 g/l ammonium acetate solution), 10% B (acetonitrile), 10% C (methanol) to 50% B and 50% C in 6.5 minutes, to 100% B at 7 minutes and equilibrated to initial conditions at 7.5 minutes until 9.0 minutes. Injection volume 5 μl. Low-resolution mass spectra (ZQ detector; quadrupole) were acquired by scanning from 100 to 1000 in 1.0 second using a dwell time of 0.3 seconds. The capillary needle voltage was 3 kV. The cone voltage was 20 V and 50 V for positive ionization mode and 20 V for negative ionization mode.

Method 5

In addition to general procedure C: Same as method 3, but using 10 μl of injection volume.

TABLE 1

Analytical Data for Compounds 66-103.

| Ex. | $R_t$ | $[M + H]^+$ | Procedure |
|---|---|---|---|
| 66 | 2.46 | 373 | 1 |
| 67 | 2.59 | 395 | 1 |
| 68 | 2.5 | 361 | 1 |
| 69 | 2.4 | 341 | 1 |
| 70 | 8.05 | 371 | 2 |
| 71 | 2.72 | 351 | 1 |
| 72 | 2.36 | 323 | 1 |
| 73 | 2.97 | 405 | 1 |
| 74 | 2.61 | 343 | 1 |
| 75 | 2.65 | 357 | 1 |
| 76 | 2.58 | 375 | 1 |
| 77 | 2.61 | 357 | 1 |
| 78 | 2.52 | 323 | 1 |
| 79 | 2.98 | 385 | 1 |
| 80 | 2.3 | 339 | 1 |
| 81 | 2.34 | 357 | 1 |
| 82 | 2.64 | 367 | 1 |
| 83 | NT | NT | NT |
| 84 | 2.98 | 389 | 1 |
| 85 | 2.95 | 369 | 1 |
| 86 | 2.25 | 352 | 1 |
| 87 | 2.71 | 395 | 1 |
| 88 | 2.62 | 388 | 1 |
| 89 | 2.78 | 385 | 1 |
| 90 | 2.99 | 421 | 1 |
| 91 | 3.02 | 379 | 1 |
| 92 | 2.43 | 407 | 1 |
| 93 | 4.2 | 373 | 3 |
| 94 | 3.57 | 339 | 4 |
| 95 | 3.14 | 376 | 3 |
| 96 | 3.84 | 359 | 3 |
| 97 | 3.78 | 357 | 3 |
| 98 | 3.98 | 365 | 3 |
| 99 | 3.1 | 376 | 5 |
| 100 | 3.59 | 339 | 3 |
| 101 | 2.38 | 401 | 1 |
| 102 | 2.45 | 362 | 3 |
| 103 | 4.01 | 396 | 3 |

NT = Not Tested

Optical Rotation

Example 100: $[\alpha]_D^{20}$ −68.15° (c 0.54 w/v %, MeOH).

Assay Methods

In Vitro Pharmacology

Stock drug solutions (10 mM) were prepared in DMSO (the final assay concentration of DMSO not exceeding 0.4%). Drug dilutions were prepared in assay buffer.

Sigmoidal inhibition curves were generated and fitted by nonlinear regression analysis (GraphPad Prism). $K_i$ values were calculated according to the Cheng and Prussoff equation (Biochem. Pharmacol. 1973, 22, 3099-3108), $IC_{50}/(1+[S]/K_d)$, where the following values were used: 5-HT$_7$ ([S]=1 nM; $K_d$=0.42); 5-HT$_{2A}$ ([S]=1 nM; $K_d$=0.4 nM); 5-HT$_{2B}$ ([S]=4 nM; $K_d$=3.5 nM); 5-HT$_{2C}$ ([S]=3 nM; $K_d$=3 nM); 5-HT$_6$ ([S]=1.7 nM; $K_d$=1.7 nM).

Data obtained for compounds tested in Assays 1-3 are presented in Table 1 below. Examples marked with an asterisk (*) were tested as their corresponding hydrochloride salt forms.

1. Affinity for 5-HT$_7$ Receptor Binding Sites

The affinity of the compounds described in this invention for the 5-HT$_7$ receptor binding site was evaluated by single competition radioligand binding assay. The assay was performed on membranes prepared from HEK-293 cells that had been subjected to stable transfection with the rat 5-HT$_{7a}$ receptor (GB: NM022938). Cells were scraped from the culture plates, suspended in Tris-HCl 50 mM pH 7.5 and collected through centrifugation (1000 rpm for 5 min). The cell pellets were homogenized (Polytron, 15 s, setting 5) in 50 mM Tris-HCl (pH 7.5), 5 mM EDTA. Following centrifugation (15,000 rpm for 25 min), membranes (135 μg protein/mL) were resuspended in the same buffer and incubated for 60 min at RT with 1 nM [$^3$H]5-CT in the presence of increasing concentration of test compounds. Nonspecific binding was defined in the presence of 10 μM 5-HT. Incubation was stopped by rapid filtration using the cell harvester (Packard). Radioactivity was counted in a TopCount-NXT (Packard). Experiments were conducted in triplicate.

2. Affinity for 5HT$_2$ Receptor Binding Sites

Receptor binding was performed using the human recombinant 5-HT$_{2A}$ (GB: X57830), 5-HT$_{2B}$ (GB: Z36748) and 5-HT$_{2C}$ (GB: M81778) receptors. The affinity of the compounds for the 3 different human 5-HT$_2$ receptor subtypes was evaluated by competitive radioligand binding assays using [$^3$H]ketanserin (h5-HT$_{2A}$) or [$^3$H]mesulergine (h5-HT$_{2B}$ and h5-HT$_{2C}$). The assays were performed on membranes prepared from NIH3T3 stably transfected with h5-HT$_{2A}$ or CHO stably transfected with h5-HT$_{2B}$ and h5-HT$_{2C}$.

3. Affinity for 5-HT$_6$ Receptor Binding Sites

Receptor binding was performed using the human recombinant 5-HT$_6$ (GB: BC0794995) receptor. The affinity of the compounds for the human 5-HT$_6$ receptor was evaluated by competitive radioligand binding assays using [$^3$H]LSD. The assays were performed on membranes prepared from HEK-293 stably transfected with h5-HT$_6$. Non-specific binding was estimated in the presence of 1 μM clozapine.

TABLE 1

| | Binding Affinities (nM) | | | | |
|---|---|---|---|---|---|
| Ex. | $K_i$ 5-HT$_7$ | $K_i$ 5-HT$_{2A}$ | $K_i$ 5-HT$_{2B}$ | $K_i$ 5-HT$_{2C}$ | $K_i$ 5-HT$_6$ |
| 1* | 470 | 20 | 32 | 300 | 2260 |
| 2* | 220 | 170 | 25 | 430 | 300 |
| 3* | 240 | 200 | 20 | 400 | 160 |
| 4* | 920 | 240 | 100 | 9000 | 3750 |
| 5* | >10,000 | 1500 | 200 | 1800 | 127 |
| 6* | >10,000 | 200 | 200 | 1000 | 310 |
| 7* | >10,000 | 400 | 280 | 3200 | 1240 |
| 8* | 500 | 180 | 100 | 2000 | 68 |
| 9* | 29 | 20 | 7 | 40 | 84 |
| 10* | 1200 | 500 | 50 | >10,000 | 1460 |
| 11* | 40 | 4 | 5 | 63 | 25 |
| 12* | 40 | 30 | 3.2 | 50 | 80 |
| 13* | 32 | 10 | 0.8 | 40 | 28 |
| 14* | 63 | 40 | 5 | 130 | 220 |
| 15* | >10,000 | NT | NT | NT | NT |
| 16* | 500 | 50 | 320 | 630 | NT |
| 17* | >10,000 | 900 | 630 | 2500 | NT |
| 18* | >10,000 | NT | NT | NT | NT |
| 19* | >10,000 | 1500 | 1000 | 3160 | NT |
| 20* | >10,000 | 300 | 790 | 6310 | NT |
| 21* | >10,000 | NT | NT | NT | NT |
| 22* | >10,000 | >10,000 | 2510 | >10,000 | NT |
| 23* | 620 | 60 | 350 | 2800 | NT |
| 24* | 50 | 3 | 7 | 120 | 933 |
| 25* | >10,000 | 190 | 620 | >10,000 | NT |
| 26* | 100 | 7 | 13 | 200 | 316 |
| 27* | >10,000 | 1700 | 660 | >10,000 | NT |
| 28* | 130 | 70 | 15 | 280 | 1514 |
| 29* | >10,000 | 650 | 1100 | >10,000 | NT |
| 30* | 300 | 48 | 60 | 1400 | 3715 |
| 31 | >10,000 | 230 | 1600 | 3200 | NT |
| 32 | 270 | 9 | 30 | 110 | NT |
| 33 | >10,000 | 540 | 800 | 3200 | NT |
| 34 | 90 | 18 | 40 | 270 | NT |

TABLE 1-continued

| | Binding Affinities (nM) | | | | |
|---|---|---|---|---|---|
| Ex. | $K_i$ 5-HT$_7$ | $K_i$ 5-HT$_{2A}$ | $K_i$ 5-HT$_{2B}$ | $K_i$ 5-HT$_{2C}$ | $K_i$ 5-HT$_6$ |
| 35 | >10,000 | >10,000 | 700 | >10,000 | NT |
| 36 | 210 | 160 | 100 | 320 | NT |
| 37 | >10,000 | 2400 | 1300 | >10,000 | NT |
| 38* | >10,000 | 1.9 | 50 | 65 | 1950 |
| 39* | 150 | 2 | 75 | 57 | 1738 |
| 40* | >10,000 | 70 | 790 | 2000 | NT |
| 41* | >10,000 | 25 | 750 | 940 | NT |
| 42* | >10,000 | 20 | 2050 | 500 | 9772 |
| 43* | 320 | 3 | 100 | 150 | 195 |
| 44* | 2000 | 9.5 | 180 | 300 | NT |
| 45* | >10,000 | 24 | 1200 | 2500 | 3388 |
| 46* | 100 | 30 | 200 | 250 | NT |
| 47 | >10,000 | 120 | 500 | 1600 | NT |
| 48 | >10,000 | 2000 | 3000 | >10,000 | >10,000 |
| 49 | 530 | 100 | 5010 | 630 | 2089 |
| 50 | 350 | 30 | 160 | 130 | 776 |
| 51 | 320 | 75 | 700 | 100 | 912 |
| 52 | >10,000 | 120 | 500 | 500 | 977 |
| 53 | NT | 2000 | 1200 | >10,000 | NT |
| 54 | 370 | 30 | 5 | 89 | NT |
| 55 | NT | 50 | >10,000 | 1100 | NT |
| 56 | 9000 | 1.4 | 45 | 40 | NT |
| 57 | NT | 500 | >10,000 | >10,000 | 2291 |
| 58 | NT | 17 | 30 | 20 | 102 |
| 59* | >10,000 | NT | NT | NT | 1479 |
| 60 | 41 | 20 | 10 | 100 | >10,000 |
| 61 | 9000 | 420 | 620 | 5000 | 2290 |
| 64 | NT | 520 | 620 | 1260 | 29 |
| 65 | NT | NT | 280 | 960 | 41 |
| 66 | NT | 61 | 8 | 46 | 47 |
| 67 | NT | NT | NT | NT | 96 |
| 68 | NT | 19 | 6 | 5 | 29 |
| 69 | NT | 35 | 5 | 5 | 13 |
| 70 | NT | 54 | 2 | 12 | 19 |
| 71 | NT | 36 | 1 | 9 | 19 |
| 72 | NT | 28 | 2 | 4 | 32 |
| 73 | NT | 170 | 7 | 38 | 62 |
| 74 | NT | 4 | 3 | 1 | 46 |
| 75 | NT | NT | NT | NT | 85.88 |
| 76 | NT | 38 | 16 | 15 | 39 |
| 77 | NT | 77 | 9 | 33 | 51 |
| 78 | NT | 2 | NT | 1 | 14 |
| 79 | NT | 39 | 7 | 26 | 18 |
| 80 | NT | 140 | 6 | 42 | 39 |
| 81 | NT | NT | NT | NT | 83 |
| 82 | NT | 48 | 3 | 17 | 35 |
| 83 | NT | 131 | 12 | 39 | 84 |
| 84 | NT | 130 | 2 | 18 | 52 |
| 85 | NT | 45 | 2 | 15 | 31 |
| 86 | NT | 660 | 9 | 240 | 80 |
| 87 | NT | NT | NT | NT | 82 |
| 88 | NT | 230 | 64 | 600 | 12 |
| 89 | NT | 180 | 3 | 33 | 35 |
| 90 | NT | NT | NT | NT | 88 |
| 91 | NT | 160 | 6 | 45 | 41 |
| 92 | NT | 1140 | 950 | 2040 | 85 |
| 93 | NT | 150 | 18 | 28 | 9 |
| 94 | NT | 25 | 15 | 15 | 8 |
| 95 | NT | 150 | 580 | 810 | 7 |
| 96* | NT | 100 | 35 | 69 | 13 |
| 97* | NT | 400 | 39 | 92 | 23 |
| 98* | NT | 99 | 25 | 140 | 13 |
| 99* | NT | 1440 | 280 | 490 | 30 |
| 100* | NT | 21 | 8 | 4 | 6 |
| 101 | NT | NT | 650 | 3780 | 92 |
| 102 | NT | NT | 300 | 360 | 70 |
| 103 | NT | NT | NT | NT | 42 |

NT = not tested

What is claimed is:

1. A compound of Formula (I):

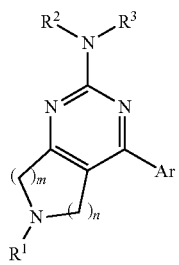

wherein
m is 1;
n is 2;
$R^1$ is —H, —$C_{1-4}$alkyl, or benzyl;
$R^2$ and $R^3$ are each independently —H, —$C_{1-4}$alkyl, or benzyl;
or alternatively, $R^2$ and $R^3$ taken together with the nitrogen to which they are attached form a saturated monocyclic heterocycloalkyl ring, unsubstituted or substituted with one or two substitutents selected from —$C_{1-4}$alkyl, —OH, and halo;
Ar is a phenyl, monocyclic heteroaryl, or bicyclic heteroaryl ring, unsubstituted or substituted with one or two $R^i$ substituents;
$R^i$ is selected from the group consisting of —$C_{1-7}$alkyl, —$C_{2-7}$alkenyl, —$C_{2-7}$alkynyl, —$C_{3-7}$cycloalkyl, halo, —$CF_3$, —OH, —$OC_{1-7}$alkyl, —$OCF_3$, —$OC_{3-7}$alkenyl, —$OC_{3-7}$alkynyl, —$N(R^j)R^k$, —$C(O)N(R^j)R^k$, —$N(R^j)C(O)R^k$, —$N(R^j)SO_2C_{1-6}$alkyl, —$S(O)_{0-2}$—$C_{1-6}$alkyl, —$SO_2N(R^j)R^k$, —$SCF_3$, —$C(O)C_{1-6}$alkyl, —$NO_2$, —CN, —COOH, and —$COOC_{1-7}$alkyl;
where $R^j$; and $R^k$ are independently —H or —$C_{1-4}$alkyl;
or alternatively, two adjacent $R^i$ substituents form —$OC_{1-4}$alkyleneO—, —$(CH_2)_{2-3}NH$—, —$(CH_2)_{1-2}NH(CH_2)$—, —$(CH_2)_{2-3}N(C_{1-4}$alkyl)-, or —$(CH_2)_{1-2}N(C_{1-4}$alkyl)$(CH_2)$—;
or a stereoisomeric form, hydrate, solvate, a pharmaceutically acceptable salt-thereof.

2. A compound as defined in claim 1, wherein $R^1$ is hydrogen, methyl, ethyl, isopropyl, butyl, or benzyl.

3. A compound as defined in claim 1, wherein $R^1$ is hydrogen or methyl.

4. A compound as defined in claim 1, wherein $R^2$ and $R^3$ are each independently hydrogen, methyl, ethyl, isopropyl, or benzyl.

5. A compound as defined in claim 1, wherein $R^2$ and $R^3$ are both ethyl.

6. A compound as defined in claim 1, wherein $R^2$ and $R^3$ taken together with the nitrogen to which they are attached form pyrrolidine, piperidine, azepane, or morpholine, unsubstituted or substituted with one or two substitutents selected from —$C_{1-4}$alkyl, —OH, and halo.

7. A compound as defined in claim 1, wherein $R^2$ and $R^3$ taken together with the nitrogen to which they are attached form pyrrolidin-1-yl, 2-methylpyrrolidin-1-yl, piperidinyl, 2-methylpiperidin-1-yl, 2,6-dimethylpiperidin-1-yl, 4-fluoropiperidin-1-yl, 4,4-difluoropiperidin-1-yl, azepan-1-yl, morpholin-4-yl, or 3-methylmorpholin-4-yl.

8. A compound as defined in claim 1, wherein Ar is phenyl, unsubstituted or substituted with one or two $R^i$ substituents.

9. A compound as defined in claim 1, wherein Ar is a monocyclic heteroaryl ring, unsubstituted or substituted with one or two $R^i$ substituents.

10. A compound as defined in claim 1, wherein Ar is a bicyclic heteroaryl ring, unsubstituted or substituted with one or two $R^i$ substituents.

11. A compound as defined in claim 1, wherein each $R^i$ substituent is selected from the group consisting of fluoro, methyl, isopropyl, methoxy, cyano, chloro, trifluoromethoxy; or two $R^i$ substituents taken together form —$OCH_2O$—.

12. A compound as defined in claim 1, wherein Ar is 4-fluorophenyl, 4-methylphenyl, 4-methoxyphenyl, 4-cyanophenyl, or 4-chlorophenyl.

13. A compound as defined in claim 1, wherein Ar is pyridyl or thiophenyl.

14. A compound as defined in claim 1, wherein Ar is quinolinyl or benzofuranyl.

15. A compound selected from the group consisting of:
[7-Benzyl-4-(4-fluoro-phenyl)-5,6,7,8-tetrahydro-pyrido[3,4-d]pyrimidin-2-yl]-diethyl-amine;
Diethyl-[4-(4-fluoro-phenyl)-5,6,7,8-tetrahydro-pyrido[3,4-d]pyrimidin-2-yl]-amine;
(7-Benzyl-4-p-tolyl-5,6,7,8-tetrahydro-pyrido[3,4-d]pyrimidin-2-yl)-diethyl-amine;
Diethyl-(4-p-tolyl-5,6,7,8-tetrahydro-pyrido[3,4-d]pyrimidin-2-yl)-amine;
[7-Benzyl-4-(4-methoxy-phenyl)-5,6,7,8-tetrahydro-pyrido[3,4-d]pyrimidin-2-yl]-diethyl-amine;
Diethyl-[4-(4-methoxy-phenyl)-5,6,7,8-tetrahydro-pyrido[3,4-d]pyrimidin-2-yl]-amine;
4-(7-Benzyl-2-diethylamino-5,6,7,8-tetrahydro-pyrido[3,4-d]pyrimidin-4-yl)-benzonitrile;
4-(2-Diethylamino-5,6,7,8-tetrahydro-pyrido[3,4-d]pyrimidin-4-yl)-benzonitrile;
4-(4-Fluoro-phenyl)-2-(2-methyl-pyrrolidin-1-yl)-5,6,7,8-tetrahydro-pyrido[4,3-d]pyrimidine;
[4-(4-Fluoro-phenyl)-5,6,7,8-tetrahydro-pyrido[4,3-d]pyrimidin-2-yl]-dimethyl-amine;
Diethyl-[4-(4-fluoro-phenyl)-5,6,7,8-tetrahydro-pyrido[4,3-d]pyrimidin-2-yl]-amine;
4-(4-Fluoro-phenyl)-2-pyrrolidin-1-yl-5,6,7,8-tetrahydro-pyrido[4,3-d]pyrimidine;
4-(4-Fluoro-phenyl)-2-morpholin-4-yl-5,6,7,8-tetrahydro-pyrido[4,3-d]pyrimidine;
[4-(4-Fluoro-phenyl)-5,6,7,8-tetrahydro-pyrido[4,3-d]pyrimidin-2-yl]-diisopropyl-amine;
Ethyl-[4-(4-fluoro-phenyl)-5,6,7,8-tetrahydro-pyrido[4,3-d]pyrimidin-2-yl]-methyl-amine;
4-(4-Fluoro-phenyl)-2-(3-methyl-morpholin-4-yl)-5,6,7,8-tetrahydro-pyrido[4,3-d]pyrimidine;
[4-(4-Chloro-phenyl)-5,6,7,8-tetrahydro-pyrido[4,3-d]pyrimidin-2-yl]-diethyl-amine;
2-Pyrrolidin-1-yl-4-p-tolyl-5,6,7,8-tetrahydro-pyrido[4,3-d]pyrimidine;
Ethyl-(4-p-tolyl-5,6,7,8-tetrahydro-pyrido[4,3-d]pyrimidin-2-yl)-amine;
2-Morpholin-4-yl-4-p-tolyl-5,6,7,8-tetrahydro-pyrido[4,3-d]pyrimidine;
2-Piperidin-1-yl-4-p-tolyl-5,6,7,8-tetrahydro-pyrido[4,3-d]pyrimidine;
Benzyl-(4-p-tolyl-5,6,7,8-tetrahydro-pyrido[4,3-d]pyrimidin-2-yl)-amine;
6-Methyl-2-pyrrolidin-1-yl-4-p-tolyl-5,6,7,8-tetrahydro-pyrido[4,3-d]pyrimidine;
and pharmaceutically acceptable salts thereof.

16. A compound as defined in claim 1, or a pharmaceutically acceptable salt thereof.

17. A pharmaceutical composition for treating a disease, disorder, or medical condition mediated by serotonin receptor activity, comprising:
  (a) an effective amount of a compound of Formula (I), or a sterioisomeric form, hydrate, solvate, pharmaceutically acceptable salt thereof; and
  (b) a pharmaceutically acceptable excipient.

18. A pharmaceutical composition according to claim 17, further comprising: an active ingredient selected from the group consisting of an additional active ingredient selected from the group consisting of: $H_1$ receptor antagonists, $H_2$ receptor antagonists, $H_3$ receptor antagonists, topiramate, norepinephrine reuptake inhibitors, selective serotonin reuptake inhibitors, noradrenergic reuptake inhibitors, non-selective serotonin re-uptake inhibitors, acetylcholinesterase inhibitors, modafinil, anti-psychotics, sedatives, monoamine oxidase inhibitors, and tricyclic antidepressants.

19. A method for treating a disease, disorder, or medical condition selected from the group consisting of: depression/anxiety, generalized anxiety disorder, schizophrenia, bipolar disorders, psychotic disorders, obsessive-compulsive disorder, post-traumatic stress migraine, appetite-stimulant, pain, insomnia, and nausea, comprising administering to a subject in need of such treatment an effective amount of a compound of Formula (I), as defined in claim 1 or a stereoisomeric form, hydrate, solvate, or pharmaceutically acceptable salt thereof.

* * * * *